(12) United States Patent
Soper et al.

(10) Patent No.: US 9,718,676 B2
(45) Date of Patent: Aug. 1, 2017

(54) POLYMERIC NANOPILLARS AND NANOTUBES, THEIR MANUFACTURE AND USES

(75) Inventors: Steven A. Soper, Baton Rouge, LA (US); Robin L. McCarley, Prairieville, LA (US); Guofang Chen, Hicksville, NY (US); Hamed Shadpour, Chapel Hill, NC (US)

(73) Assignee: Board of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 2114 days.

(21) Appl. No.: 12/440,546

(22) PCT Filed: Sep. 12, 2007

(86) PCT No.: PCT/US2007/078255
§ 371 (c)(1),
(2), (4) Date: Nov. 12, 2009

(87) PCT Pub. No.: WO2008/097360
PCT Pub. Date: Aug. 14, 2008

(65) Prior Publication Data
US 2010/0108519 A1 May 6, 2010

Related U.S. Application Data

(60) Provisional application No. 60/844,506, filed on Sep. 14, 2006.

(51) Int. Cl.
*B82B 3/00* (2006.01)
*G01N 27/26* (2006.01)
*G01N 33/561* (2006.01)
*B81C 1/00* (2006.01)
*G01N 27/447* (2006.01)

(52) U.S. Cl.
CPC .... *B81C 1/00111* (2013.01); *G01N 27/44773* (2013.01); *B81C 2201/034* (2013.01); *Y10T 428/2982* (2015.01)

(58) Field of Classification Search
CPC .... B82B 3/00; G01N 27/26; G01N 27/44791; G01N 33/561
See application file for complete search history.

(56) References Cited

U.S. PATENT DOCUMENTS

| | | | |
|---|---|---|---|
| 6,664,104 B2 | 12/2003 | Pourahmadi et al. | 435/288.6 |
| 6,685,841 B2 * | 2/2004 | Lopez | B01L 3/502746 137/833 |
| 2003/0089605 A1 * | 5/2003 | Timperman | 204/450 |
| 2006/0119015 A1 * | 6/2006 | Wehrspohn et al. | 264/627 |
| 2006/0289351 A1 | 12/2006 | Xiao et al. | 210/500.25 |

OTHER PUBLICATIONS

Chen, X. et al., "A Prototype Two-Dimensional Capillary Electrophoresis System Fabricated in Poly(dimethylsiloxane)," Anal. Chem, vol. 74, pp. 1772-1778 (2002).
Chen, G. et al., "Free-standing, erect ultra-high-aspect-ratio polymer nanopillar and nanotube ensembles," Langmuir, vol. 23, pp. 11777-11781 (2007).
Chen, G. et al. "Functional template-derived poly(methyl methacrylate) nanopillars for solid-phase biological reactions," Chemistry of Materials, vol. 19, No. 16, pp. 3855-3857 (2007).
Chen, G. et al., "Integration of large-area polymer nanopillar arrays into microfluidic devices using in situ polymerization cast molding," Lab on a Chip, vol. 7, pp. 1424-1427 (2007).
Demianova, Z. et al., "Toward an Integrated Microchip Sized 2-D Polyzcrylamide Slab Gel Electrophoresis Device for Proteomic Analysis," Electrophoresis, vol. 28, pp. 442-428 (2007).
Duan, J. et al., "Rapid protein digestion and identification using monolithic enzymatic microreactor coupled with nano-liquid chromatography-electrospray ionization mass spectrometry," J. Chrom. A, vol. 1106, pp. 165-174 (2006).
Foote, R. et al., "Preconcentration of proteins on microfluidic devices using porous silica membranes," Anal. Chem., vol. 77, pp. 57-63 (2005).
Gottschlich et al., "Two-dimensional Electrochromatography/Capillary Electrophoresis on a Microchip", Analytical Chemistry, vol. 73, No. 11, Jun. 1, 2001, pp. 2669-2674.
Griebel, A. et al., "Integrated Polymer Chip for Two-Dimensional Capillary Gel Electrophoresis," Lab Chip, vol. 4, pp. 18-23 (2004).
Herr, A.E. et al., "On-Chip Coupling of Isoelectric Focusing and Free Solution Electrophoresis for Multidimensional Separations," Anal. Chem., vol. 75, pp. 1180-1187 (2003).
Kaji, N. et al., "Separation of long DNA molecules by quartz nanopillar chips under a direct current electric field," Anal. Chem., vol. 76, pp. 15-22 (2004).

(Continued)

*Primary Examiner* — Randy Boyer
(74) *Attorney, Agent, or Firm* — John H. Runnels

(57) ABSTRACT

A method is disclosed for fabricating free-standing polymeric nanopillars or nanotubes with remarkably high aspect ratios. The nanopillars and nanotubes may be used, for example, in integrated microfluidic systems for rapid, automated, high-capacity analysis or separation of complex protein mixtures or their enzyme digest products. One embodiment, preferably fabricated entirely from polymer substrates, comprises a cell lysis unit; a solid-phase extraction unit with free-standing, polymeric nanostructures; a multi-dimensional electrophoretic separation unit with high peak capacity; a solid-phase nanoreactor for the proteolytic digestion of isolated proteins; and a chromatographic unit for the separation of peptide fragments from the digestion of proteins. The nanopillars and nanotubes may also be used to increase surface area for reaction with a solid phase, for example, with immobilized enzymes or other catalysts within a microchannel, or as a solid support for capillary electrochromatography-based separations of proteins or peptides.

8 Claims, 12 Drawing Sheets

(56) References Cited

OTHER PUBLICATIONS

Li, Y. et al., "Integration of Isoelectric Focusing with Parallel Sodium Dodecyl Sulfate Gel Electrophoresis for Multidimensional Protein Separations in a Plastric Mocrofluidic Network," Anal. Chem., vol. 76, pp. 742-748 (2004).
Liu, J. et al., "Surface-modified poly(methyl methacrylate) capillary electrophoresis microchips for protein and peptide analysis," *Anal. Chem.*, vol. 76, pp. 6948-6955 (2004).
Osiri, J.K. et al., "Generating High Peak Capacity 2-D Maps of Complex Proteomes Using PMMA Microchip Electrophoresis," Electrophoresis, vol. 29, pp. 4984-4992 (2008).
Ramsey et al. for peptides using fluorescence detection on a glass microchip, Analytical Chemistry, vol. 75, pp. 3758-3764 (2003).
Rocklin et al., "A Microfabricated Fluidic Device for Performing Two-Dimensional Liquid-Phase Separations", Analytical Chemistry, vol. 72, No. 21, pp. 5244-5249 (2000).
Shadpour, H. et al., "Two-dimensional electrophoretic separation of proteins using poly(methyl methacrylate) microchips," *Analytical Chemistry*, vol. 78, pp. 3519-3527 (2006).
Slovakova, M. et al., "Use of self assembled magnetic beads for on-chip protein digestion," *Lab Chip*, vol. 5, pp. 935-942 (2005).
Sluszny, C. et al., "One- and Two-Dimensional Miniaturized Electrophoresis of Proteins with Native Fluorescence Detection," Anal. Chem., vol. 76, pp. 1359-1365 (2004).
Wang, Y-C et al., "Two-Dimensional Protein Separation with Advanced Sample and Buffer Isolation Using Microfluidic Valves," Anal. Chem., vol. 76, pp. 4426-4431 (2004).
Xu, A. et al., "Protype for Integrated Two-Dimensional Gel Electrophoresis for Protein Separation," J. of Chrom. A, vol. 1087, pp. 177-182 (2005).

\* cited by examiner

POLYMERIC NANOPILLARS AND NANOTUBES, THEIR MANUFACTURE AND USES

This is the United States national stage of international application PCT/US2007/078255, international filing date 12 Sep. 2007, which claims the benefit of the 14 Sep. 2006 filing date of U.S. provisional patent application Ser. No. 60/844,506 under 35 U.S.C. §119(e).

The Development of this invention was partially funded by the United States Government under grants DBI-0138048 and EPS-0346411 awarded by the National Science Foundation. The United States Government has certain rights in this invention.

TECHNICAL FIELD

This invention pertains to polymeric nanopillars and nanotubes, their manufacture, and their uses in chemical and biological separations, analyses, and reactions.

BACKGROUND ART

The "proteome" is the complete set of proteins expressed by a cell or population of cells. "Proteomics" is the study of proteomes. An essential step in proteomics is the isolation and identification of the proteins that are being expressed at a particular time, preferably over a range of conditions such as different ages; disease states; and differing exposures to environmental factors such as temperatures, nutrient levels, pharmaceuticals, and other chemical compounds. Quantitative comparisons of protein concentrations under different conditions yield important insights about the health of the organism. For example, there are "marker proteins" whose concentrations change during the progression of disease. Marker proteins have been identified for ailments including many cancers, Alzheimer's disease, schizophrenia, and Parkinson's disease. The accurate measurement of these markers is becoming increasingly important in clinical assays for human disorders and diseases, and can lead to treatments and even cures for a range of maladies.

There are several methods in common use for analyzing complex protein mixtures such as a proteome. In a common strategy the protein mixture is fractionated into individual units, typically using two-dimensional (2D) gel electrophoresis. Proteins are first separated in one dimension, usually by isoelectric focusing (IEF) along a gradient of electrical potential. Each protein's electric charge, which is a function of its constituent amino acids, post-translational phosphorylation, glycosylation, etc., drives the protein along the potential gradient until it reaches its uncharged isoelectric point (pI). The one-dimensional (1D), pI-focused linear array of proteins is then subjected to gel electrophoresis by applying a large electric field in a perpendicular direction. The proteins are driven electrophoretically by the electric field, and separate according to their electrophoretic mobilities, which in turn are determined principally by a protein's size.

Although 2-D gel electrophoresis can resolve more than 1,000 proteins in a single analysis, it has significant limitations. First, its resolving power may be orders of magnitude too small for proteomics, because the sheer number of distinct proteins present in a sample could be on the order of 1,000,000. (The human proteome has been estimated to contain 1.5 million distinct proteins.) Further complexity arises from the numerous interactions that occur among proteins, and between proteins and other ligands. Additionally, proteins are often modified by reactions such as phosphorylation, glycosylation, carbamylation, deamidation, and truncation.

Current bench top electrophoresis methods can be subject to run-to-run reproducibility problems, which can make it difficult to resolve or compare differences between two different gels, whether or the same or different specimens. The ability to make accurate comparisons is particularly important when comparing diseased and healthy specimens, where differences can be subtle; or when comparing the proteome of an organism when it is subjected to different environments or drug exposures.

A typical analysis involves several time-consuming, labor-intensive, skilled operations. For example, 2D gel electrophoresis typically requires several days of development time, followed by staining the gel to visualize proteins, picking "protein spots" from the gel for enzymatic digestion, separating the resulting peptide fragments, and mass spectrometry (MS) to identify those fragments.

Another challenge in protein separation is that the concentrations of different proteins can vary enormously, sometimes by up to ten orders of magnitude. An important consequence of the wide concentration range is that different stains are typically used to visualize spots within a gel plate. The stains have differing sensitivities to protein structures and concentrations, and are not reliably quantitative. Stain variability may affect subsequent analysis, e.g., an excised, stained gel spot subjected to mass spectrometry may yield different results depending upon the nature of the stain-protein interaction, which may be irreproducible from gel-to-gel.

Because of the difficulties and limitations in analyzing proteins by conventional, bench-top processing techniques for proteomic studies, there is an unfilled need for alternative techniques to analyze proteins, mixtures of proteins, and proteomes.

The peak capacity, P, refers to the maximum number of components that can be resolved in any one separation. A requirement of any successful multi-dimensional procedure is orthogonality, which means that the selected single dimensions possess different but compatible separation mechanisms. Furthermore, any separation step in a series of separations should not un-do any separations that were achieved by prior steps. When separation modes are truly orthogonal, the peak capacity P of a multi-dimensional separation is the product of the n peak capacities of its constituent 1D methods, $P=P_1 \times P_2 \times \ldots P_{n-1} \times P_n$. Complete orthogonality is rarely obtained with any multi-dimensional separation technique; i.e., the peak capacity found in practice is generally lower than the theoretical maximum.

Microfluidic devices have been used to implement various separation techniques. Typically, microfluidic devices apply an electric field to induce or to switch fluid flow. To achieve reproducible, high-resolution separations, it should be possible to controllably inject a fluid sample "plug," a predetermined volume of fluid sample, into a separation conduit. For fluid samples containing high molecular weight, charged biomolecules such as proteins, microfluidic devices containing an electrophoresis separation channel a few millimeters to a few centimeters long may be used to separate small fluid samples having a plug length on the order of a few micrometers. High-sensitivity detection techniques such as laser-induced fluorescence (LIF) may be used to monitor separated sample components. The analyte stream may also be fed into other analytical devices such as a mass spectrometer for detailed characterizations. Microfluidic devices have been reported for 2D separations using IEF and sodium dodecyl sulfate polyacrylamide gel electrophoresis (SDS-PAGE), electrophoretic peptide separations, solid-phase digestion using enzymatic bioreactors, and interfacing to either matrix-assisted laser desorption/ionization (MALDI) or electrospray ionization (ESI) mass spectrometry.

Recently, on-line 2D capillary electrophoresis (CE) has been reported, with high separation efficiencies, good resolution and convenient coupling to MS. Other 2D CE techniques have included coupling of isotachophoresis (ITP) and capillary zone electrophoresis (CZE), IEF, and ITP, CZE and capillary gel electrophoresis (CGE), capillary sieving electrophoresis (CSE) and micellar electrokinetic chromatography (MEKC), MEKC and IEF, IEF and CGE, IEF and CSE, and CE and CZE. These 2D CE separations typically have peak capacities in the range of 500-1,000.

Microchip capillary electrophoresis (μ-CE) represents a promising avenue for proteome analysis, offering advantages such as reduced consumption of sample and reagents, shorter analysis times, low "dead" volumes when multiple separation techniques or "dimensions" are coupled, and the ability to integrate complex geometries into a small area. In addition, microchips may be fabricated in a variety of polymer substrates suitable for different separations, using a single replication master. *Journal of Chromatography A* 2006, 1111 238-251.

However, only a few successful instances of 2D μCE separations have previously been reported. On-chip 2D CE separations were described by Ramsey et al. for peptides using fluorescence detection on a glass microchip. *Analytical Chemistry* 2003, 75, 3758-3764; *Analytical Chemistry* 2001, 73, 2669-2674; *Analytical Chemistry* 2000, 72, 5244-5249. The proteins were digested into peptides off-chip prior to conducting the separation. 2D μ-CE separations of proteins without prior digestion have been reported by coupling IEF with CZE, or IEF with CGE. *Analytical Chemistry* 2003, 75, 1180-1187; *Analytical Chemistry* 2004, 76, 4426-4431; *Lab on a Chip* 2004, 4, 18-23; *Analytical Chemistry* 2004, 76, 4426-4431; *Analytical Chemistry* 2004, 76, 742-748; *Analytical Chemistry* 2004, 76, 1359-1365; *Analytical Chemistry* 2002, 74, 1772-1778; *Journal of Chromatography, A* 2005, 1087, 177-182; *Electrophoresis* 2007, 28, 422-428.

Most prior 2D separations of proteins on microchips have used IEF as one of the separation dimensions. However, IEF is generally incompatible with fluorescence labeling, because the incorporation of a fluorescent tag will generally alter a molecule's isoelectric point. Furthermore, diffusion between focused bands following IEF decreases the efficiency and resolution following transfer into the second dimension. Some investigators have reported low reproducibility in the IEF dimension.

A capillary electrochromatography device can be made by placing a high surface-area stationary or pseudo-stationary phase in an electrophoresis microchannel. Electroosmotic flow (EOF) drives the mobile liquid phase through the channel, and analyte-stationary phase interactions lead to different analyte retention times in the microchannel. A modification is to make the high surface-area stationary phase reactive, e.g., by attaching an enzyme or other catalyst to digest larger protein molecules into smaller, more easily identifiable polypeptides.

H. Shadpour et al., "Two-dimensional electrophoretic separation of proteins using poly(methyl methacrylate) microchips," *Analytical Chemistry,* 2006, 78, 3519-3527 discloses 2D electrophoretic separations of proteins in a poly(methyl methacrylate)-(PMMA-) based microchip. Sodium dodecyl sulfate microcapillary gel electrophoresis (SDS μ-CGE) and MEKC were used as the separation modes. The microchip was prepared by hot embossing into PMMA from a brass mold master fabricated via high-precision micromilling. The microchip incorporated a 30-mm SDS μ-CGE and a 10-mm MEKC dimension.

G. Chen et al., "Functional template-derived poly(methyl methacrylate) nanopillars for solid-phase biological reactions," *Chemistry of Materials, vol.* 19, pp. 3855-3857 (2007) discloses the fabrication of ultra-high aspect ratio polymer nanopillars by a template-synthesized approach, and their use as high surface area scaffolds for attaching biomolecules. See also G. Chen et al., "Free-standing, erect ultra-high-aspect-ratio polymer nanopillar and nanotube ensembles," *Langmuir* (accepted for publication, 2007).

U.S. patent application publication 2003/0089605 discloses a microfluidic system and method to analyze large numbers of compounds, using an upstream separation module (such as a multidimensional separation device), a microfluidic device for on-device protein digestion of substantially separated proteins received from the upstream separation module, a downstream separation module for separating digestion products of the proteins, a peptide analysis module, and a processor for determining the amino acid sequence of the proteins.

N. Kaji et al., "Separation of long DNA molecules by quartz nanopillar chips under a direct current electric field," *Anal. Chem., vol.* 76, pp. 15-22 (2004) discloses the production of $SiO_2$ nanopillars by a dry etching process. The nanopillars were employed in a channel to separate DNA fragments. The nanopillars were reported to have a diameter 100-500 nm, and a height 500-5000 nm.

M. Slovakova et al., "Use of self assembled magnetic beads for on-chip protein digestion," *Lab Chip, vol.* 5, pp. 935-942 (2005) discloses the use of grafted trypsin magnetic beads for protein digestion in a PDMS microchannel.

J. Duan et al., "Rapid protein digestion and identification using monolithic enzymatic microreactor coupled with nano-liquid chromatography-electrospray ionization mass spectrometry," *J. Chrom. A, vol.* 1106, pp. 165-174 (2006) discloses an enzymatic microreactor prepared in a fused-silica capillary by in situ polymerization of acrylamide, N-acryloxysuccinimide, and ethylene dimethacrylate in the presence of a binary porogenic mixture of dodecanol and cyclohexanol; and the use of the microreactor for the digestion of cytochrome c over immobilized trypsin.

R. Foote et al., "Preconcentration of proteins on microfluidic devices using porous silica membranes," *Anal. Chem., vol.* 77, pp. 57-63 (2005) discloses the electrophoretic concentration of proteins on a microfabricated device using a porous silica membrane between microchannels, followed by separation in a coated or uncoated channel.

J. Liu et al., "Surface-modified poly(methyl methacrylate) capillary electrophoresis microchips for protein and peptide analysis," *Anal. Chem., vol.* 76, pp. 6948-6955 (2004) discloses the use of surface-modified PMMA for capillary electrophoresis.

There is a continuing, unfilled need for high-surface-area solid supports for protein digestion, analysis, and other uses. Supports that have been used include gel pads, beads, monoliths, and lithographically fabricated micro- and nano-pillars. Nanopillars in particular have the potential to be useful. Their height, aspect ratio, and spacing can be selected to match the biological reagents, diffusion attributes, and other factors to the particular need. However, prior methods for producing nanopillars are expensive and have low throughput. Templates have been used to form polymers into ordered pillar arrays, but this technique has not successfully produced small-diameter nanopillars (diameter less than about 500 nm) with the aspect ratios higher than about 2-5; and the ability to withstand the solution processing conditions required to attach chemical or biological compounds onto them.

DISCLOSURE OF THE INVENTION

We have discovered a method to fabricate free-standing polymeric nanopillars or nanotubes with remarkably high aspect ratios. Small diameter nanopillars (less than about 500 nm, 200 nm, 100 nm, in diameter, down to about 60 nm diameter) have been made with aspect ratios higher—in some cases orders of magnitude higher—than has been achieved in the prior art, aspect ratios of 10, 50, 100, 200, 500, 1000, 1500, even up to 1600. The novel nanopillars and nanotubes have many uses. They may be used, for example, in integrated microfluidic systems for rapid, automated, high-capacity analysis or separation of complex protein mixtures or their enzyme digestion products. The microfluidic devices may be used independently, or as modules in an integrated system. The analyte stream from the device may be identified by means known in the art, such as MS. One embodiment, preferably fabricated entirely from polymer substrates, comprises a cell lysis unit; a solid-phase extraction unit with free-standing, polymeric nanostructures; a multi-dimensional electrophoretic separation unit with high peak capacity; a solid-phase nanoreactor comprising nanopillars for the proteolytic digestion of isolated proteins; and a chromatographic unit for the separation of peptide fragments from the digestion of proteins. The nanopillars and nanotubes of this invention may also be used to increase surface area for reaction with a solid phase, for example, with immobilized enzymes or other catalysts within a microchannel. The nanostructures may optionally be used in the separation and digestion units as well.

In one embodiment, we first form a template of anodic aluminum oxide (AAO), and then form and polymerize polymer around the template. Anodic aluminum oxide is preferred for use in this invention over other forms of aluminum oxide due to its crystal structure. After polymerization the AAO template is removed using a low-strength etching agent, such as dilute phosphoric acid or other weak acid, and solvent is then removed by supercritical drying or freeze-drying. This embodiment is depicted in FIG. 5.

Note that, unless context suggests otherwise, the term "diameter" in the specification and the claims refers to the longest dimension across an object or across the object's cross-section, and that the term "diameter" does not imply that the object or its cross-section is necessarily circular.

MODES FOR CARRYING OUT THE INVENTION

Figure 1:
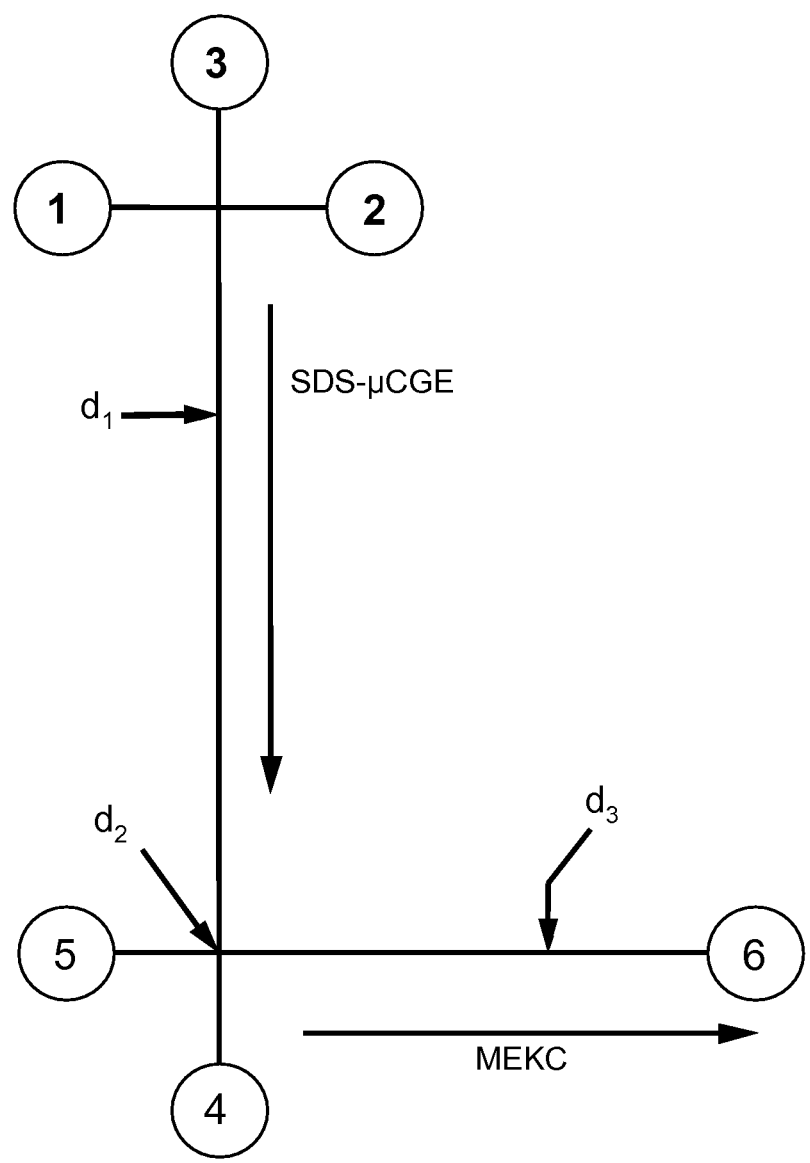
FIG. 1 depicts schematically a layout of an embodiment of a micro-electrophoresis chip used for 1D and 2D separations. The solution reservoirs depicted include: (1) sample reservoir, (2) sample waste reservoir, (3) SDS μ-CGE buffer reservoir, (4) SDS μ-CGE buffer waste reservoir, (5) MEKC buffer reservoir, and (6) MEKC buffer waste reservoir.

We have used template-based methods to make polymeric, ultra-high aspect ratio nanopillars and (PUHARNs) from PMMA or cyclic olefin copolymers (COC) such as Topas 6013D61 (TOPAS Advanced Polymers GmbH, Florence, Ky.). We have manufactured PUHARNs with ultra-high-aspect ratios R, up to R≈1,600, where R=height/diameter. The PUHARN devices may be used alone, or as a module or portion of a module in an integrated microdevice. The high aspect ratio helps keep the "footprint" of an extraction/reactor bed small, so that other processing units may be located on the same wafer. Three important factors in using the fabrication process are: (1) control over the type of architecture to be produced (nanopillar or nanotube), (2) facilitating template filling by appropriate selection of the precursor material, to conform the pillars or tubes to the template's contour, and (3) the physical integrity of the polymeric nanostructures after removal of the template.

The aspect ratio for polymeric nanopillars is limited both by the template fabrication method, and the potential for structural collapse of the features following release from the template. We discovered, unexpectedly, that surface tension effects from the solvent play an important role in the maintenance or collapse of the high aspect ratio microstructures. We also discovered, unexpectedly, that the manner of removing the template plays a major role as well. We have prepared upright, free-standing nanopillars of PMMA with remarkably high aspect ratios by polymerization onto an anodic aluminum oxide (AAO) template, followed by careful removal of the AAO template with a low-strength etching agent such as dilute phosphoric acid, and subsequent freeze-drying to remove solvent while avoiding surface tension-related effects. An embodiment of the fabrication process is illustrated schematically in FIG. 5.

When we instead removed the AAO template by the more conventional route of dissolving with sodium hydroxide, followed by ambient removal of solvent, the result was the complete collapse of the nascent nanostructures. We found that the combination of dilute phosphoric acid as an AAO template etching agent and freeze-drying to remove solvent allowed us to produce upright, ordered nanopillars that did not collapse, nanopillars having aspect ratios ranging from 5.7 (1 µm height, 460 nm center-to-center spacing) to 343 (60 µm height, 460 nm center-to-center spacing). While freeze-drying is preferred to remove solvent without adverse surface tension effects, supercritical drying can also be used. As another alternative, if the nanostructures are maintained in liquid and not allowed to dry, adverse surface tension effects can also be avoided.

We have made microchannels (50 µm wide, 50 µm deep and 50 mm long) containing free-standing PMMA nanopillars. The surfaces of the nanopillars may be derivatized with biomolecules or other chemical compounds, without mechanical damage to the nanopillars. As compared to a planar surface, the 5.7 aspect ratio nanopillars increased the available surface area by a factor of about 4, while the 343 aspect ratio nanopillars increased the available surface area by a factor of about 343.

We have obtained even higher aspect ratios R, up to 1670 (60-nm diameter, 100 µm height) with cyclic olefin copolymer (COC).

The enhanced surface area makes the arrays of the nanopillars ideal for supporting chemical or biological reactions at the solution-solid interface. For example, they may be used to increase immobilized enzyme load in solid-phase bioreactors, as well as reducing diffusional distances to increase reaction rates. In a test of one embodiment, the magnitude of the apparent kinetic parameter, $V_{max}$, was ~10-times greater for trypsin immobilized onto PMMA nanopillars as compared to a PMMA planar support.

In another test we demonstrated the solid-phase proteolytic digestion of two proteins, myoglobin and cytochrome C. Fourteen peptide fragments were generated from myoglobin, and eleven were generated from cytochrome C.

Microfluidic devices can be relatively inexpensive to manufacture. However, their production presents some unique challenges. For example, flow characteristics in the small channels of a microfluidic device differ from the flow characteristics of fluids in larger devices. Surface effects predominate, and the regions of bulk flow become proportionately much smaller. Small variations in the dimensions of a microchannel can have substantial effects on device performance, so tolerances must be comparatively tight when microfluidic devices are mass-produced. A 2D integrated protein processing chip containing nanopillar arrays in accordance with the present invention can be readily mass-produced by hot-embossing and template-directed polymerization, respectively. They may optionally be integrated into a single monolithic chip, which may also include other components known in the art.

The structures are optionally functionalized. A preferred technique for functionalization uses UV-activation to produce a structurally undamaged nanopillar or nanotube. The UV-activated nanostructure is then further modified by chemical treatment of the photo-oxidized surface. The derivatized nanopillars have unique advantages. For example, in solid-phase or heterogeneous reactions, advantages include: high target binding/loading capacity, rapid kinetics, and a dimensionally-favorable microenvironment that enhances the structural stability of bound compounds (e.g., enzymes or other catalysts).

The ease with which nanopillars can be made through the novel technique, their ready chemical and biological modification, the ability to pattern them over large areas, and the possibility of integrating them into microfluidic networks via simple micromachining methods known in the art will provide mixed-scale devices with high functionality have been difficult or impossible to produce using prior nanofabrication techniques.

Example 1. Integrated Protein Analysis System
Overview

Figure 10:
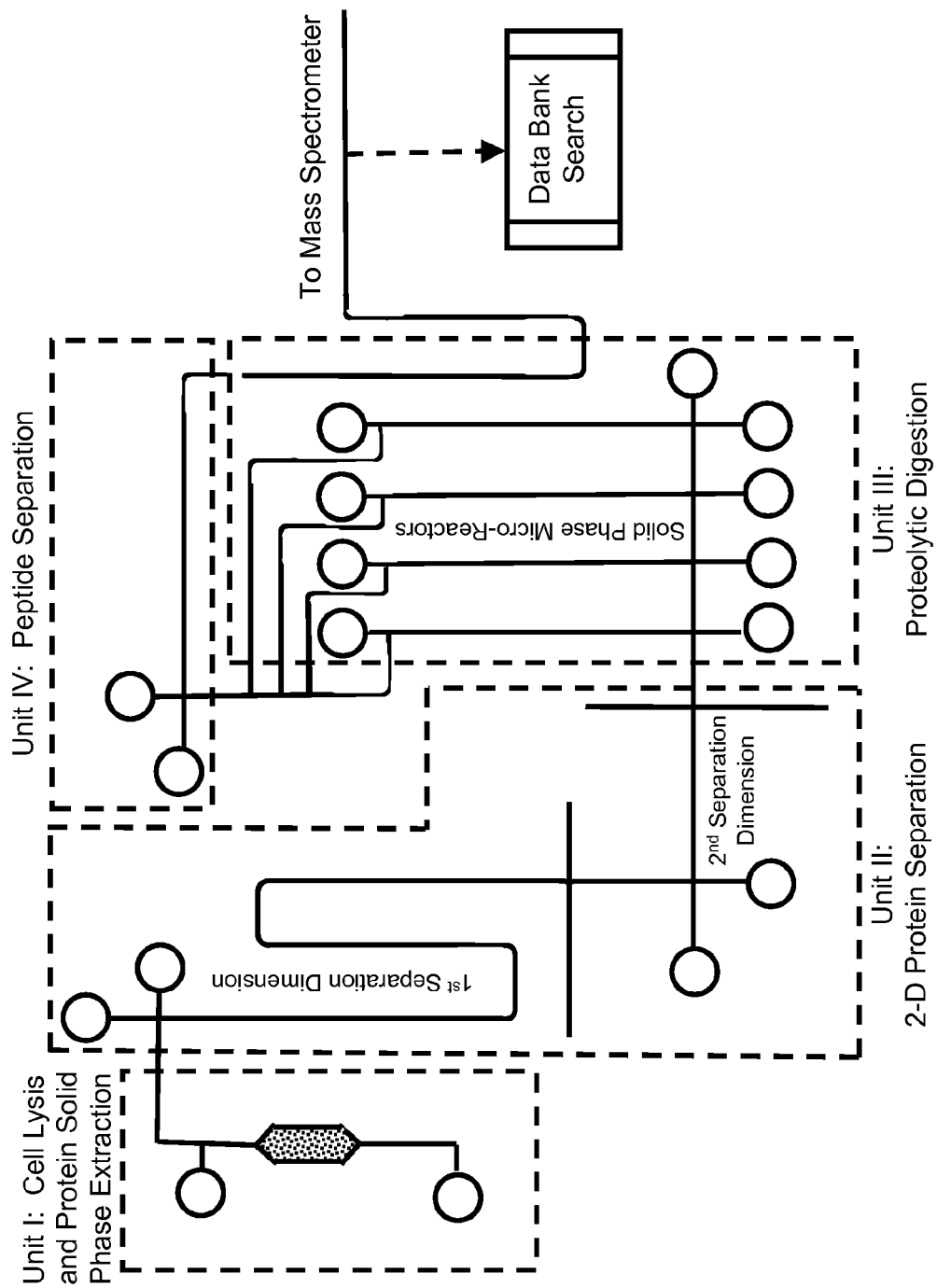
FIG. 10 depicts schematically an integrated microfluidic chip suitable, for example, for complete proteomic analyses.

There is an unfilled need for a unitary system for profiling proteins, a system in which the processing steps are seamlessly integrated, and whose output may be interfaced to a mass spectrometer or other analytic instrument. One embodiment of the invention employs the novel nanoarrays in an integrated microfluidic system that can select a subpopulation of proteins from whole cell lysates and process these proteins directly on-chip, in a fully automated fashion, much faster than previous state-of-the-art systems have been able to achieve. A prototype embodiment of such a system has been fabricated via micro-replication technologies in PMMA. PMMA was chosen since its surface may readily be modified chemically, and since it has shown excellent performance in a variety of micro-separation formats. A schematic of the integrated system is shown in FIG. 10. In a preferred embodiment the system includes subunits for the selective capture of different target protein populations (e.g., cationic, anionic, hydrophobic, hydrophilic, etc); 2D separation; solid-phase proteolytic digestion; and 1D separation of the generated peptide fragments. The system can readily be interfaced to either ESI or MALDI mass spectrometry if desired. Polymers are advantageous materials for microfluidic chips because of the flexibility in micro-manufacturing polymer chips, and the low cost of replicating chips from masters using either hot-embossing or injection molding. Additionally, there is a wide choice of modification chemistries for polymers for various applications. For example, Shadpour et al., *Journal of Chromatography A* 2006, 1111 238-251 reported the physiochemical properties of sixteen different polymers that might be used in microchip separations. Examples of other polymers that might be used in practicing this invention include others that could be photopolymerized or embossed, including polycarbonates, polyacrylates, polyimides, polyesters, polysulfones, polyethylenes and other polyalkenes, polyurethanes, polyepoxides, poly(dimethylsiloxane) and SUB. Other solution-phase or gas-phase modification chemistries known in the art may be used for surface modifications.

As used in the specification and claims a "synthetic polymer" refers to a polymer that is artificially synthesized, and that differs chemically from any polymer that is known to be formed naturally by living organisms. The term "synthetic polymer" is not intended to include a polymer that is chemically identical to a polymer known to be formed naturally by living organisms, even if synthesized by artificial means in a particular instance.

In a preferred embodiment active components such as valves are eliminated. Sample transport from unit-to-unit, and other transport functions are electrokinetically actuated. Electrokinetic flow is a composite of both the substrate's EOF, and the electrophoretic mobility of the components in solution. A large EOF can be generated at selected regions of the system using polymer modification chemistries to assure unidirectional flow of all components. Protein samples are dispensed into the sample reservoir (1) and electrokinetically driven through the solid-phase extraction bed towards the waste reservoir (2). (See FIG. 10.) After release of proteins from the extraction bed, the sample is electrokinetically injected into the separation column of the first dimension of separation. The progress of this separation is monitored, for example with a conductivity detector at the end of this column (point $d_1$), to facilitate synchronized insertion of components into the second dimension of the unit. Individual components sorted in the second dimension are isolated and sent to separate digestion beds for proteolytic digestion. A detector, e.g. another conductivity detector ($d_2$), is placed at the end of this column to direct individual protein bands into the appropriate digestion bed (preferably, 1 bed per component). As the separation proceeds in the second dimension, components from the first separation dimension are temporarily parked as needed. Multiple digestion beds may be incorporated into the system as desired for a particular application. Following digestion, peptides are pre-concentrated, for example, using an electrocapture method, separated, and detected, for example, by conductivity measurements.

Electrical signals from the conductivity detectors and from the high-voltage electrophoresis power supply are interfaced to the microfluidic chip through a printed circuit board (PCB). The PCB has spring-loaded Au-coated pins to connect the conductivity detection unit to the conductivity connector pads patterned on the cover plate of the microfluidic chip, and platinum (Pt) wire electrodes to distribute high voltage to all fluidic reservoirs used for capillary electrophoresis. Optionally, power may be supplied to all reservoirs through a metallic network (e.g., Au, Pt, or Pd) patterned onto the cover plate of the microchip.

Advantages of the novel system include the following: It may be molded from inexpensive polymers in a single step. It can be fabricated to be highly integrated. No staining or other labeling is required for detection. It may be adapted for low throughput (e.g., 1 sample, 1 wafer), or high throughput modes (e.g., many samples, modular format). Its output may be directly interfaced to a wide variety of mass spectroscopes or other instruments known in the art.

Example 2. Fabrication of Polymeric Nanopillars

Figure 5:
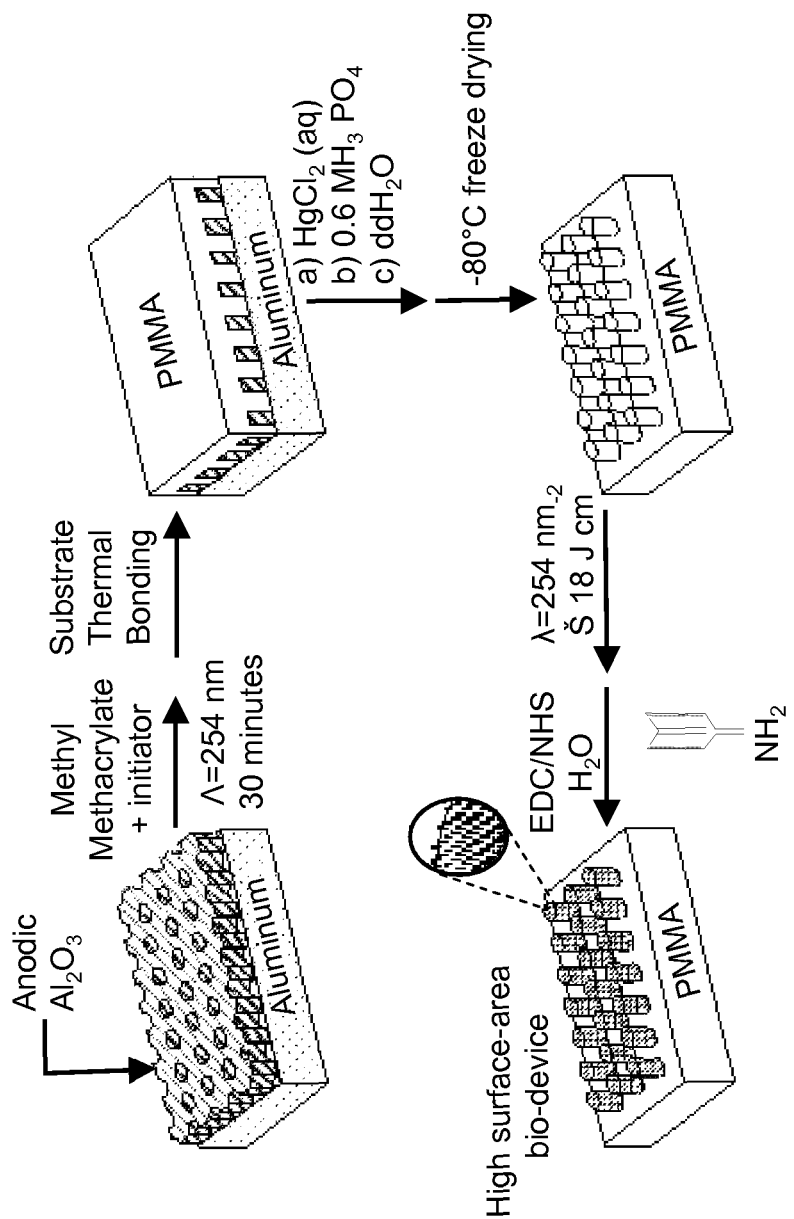
FIG. 5 depicts schematically the fabrication and functionalization of free-standing PMMA nanopillar surfaces in accordance with the present invention.
Figure 6:
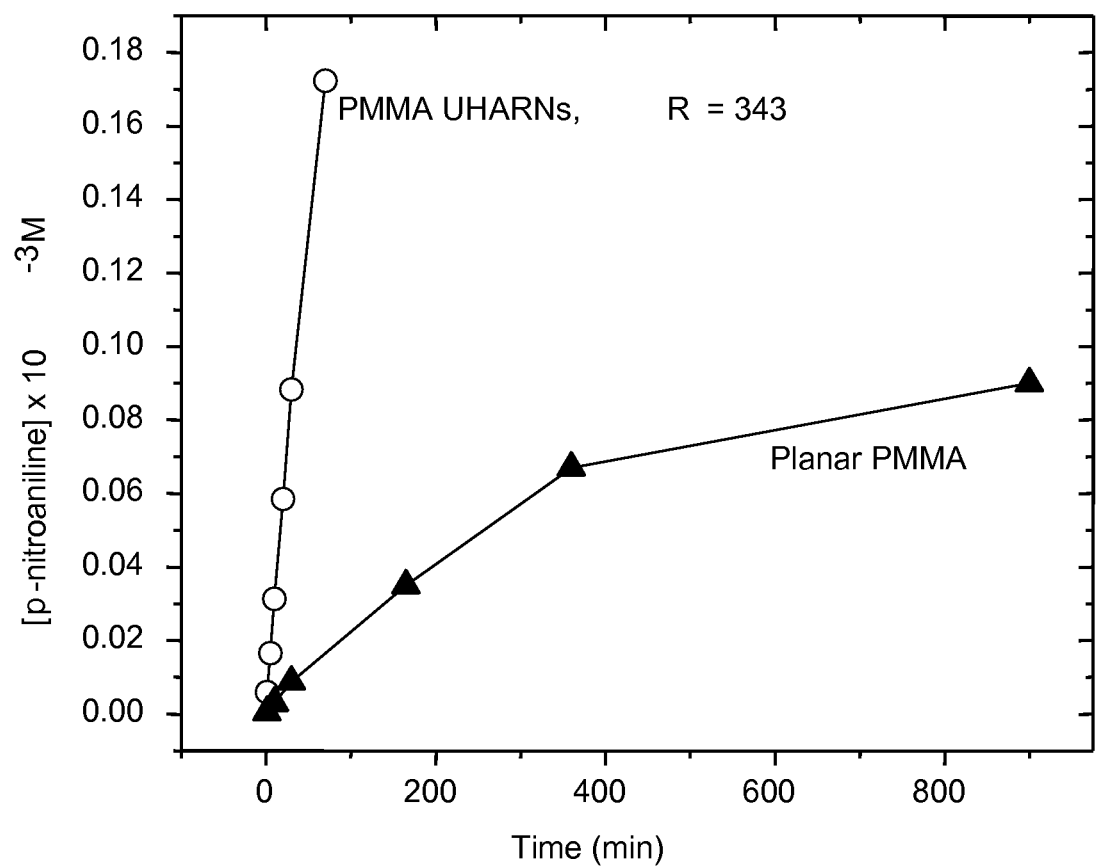
FIG. 6 depicts the formation of p-nitroaniline from the digestion of solution-phase N-benzoyl-L-arginine-p-nitroanilide ($1 \times 10^{-3}$ M) by covalently attached trypsin on PUHARN and planar PMMA substrates at 25° C.

The fabrication process is illustrated schematically in FIG. 5. Anodized aluminum oxide (AAO) templates were prepared via a two-step anodization process. The AAO templates comprised an Al substrate with an AAO layer having nanochannels open on one end. Methyl methacrylate (MMA) monomer (Fisher Scientific, Pittsburgh, Pa.) containing 1% w/v benzoin methyl ether (Fisher Scientific, Pittsburgh, Pa.), and 1% w/v PMMA (Mw 93,300 and Mn 46,400; Scientific Polymer Products Inc., Ontario, N.Y.; CAT#037Sb) was introduced into the nanochannels of the AAO templates by ultrasonicating (Branson Ultrasonic Cleaner Model 2510) the template and the methyl methacrylate/benzoin methyl ether/MMA solution for 30 min. The sample was then immediately placed on a glass support, either under laboratory ambient atmosphere or under $N_2$, and polymerization was induced by a 30-min exposure to 254-nm UV (15 mW/cm$^2$, DUV Exposure System, ABM, Inc., San Jose, Calif.). Subsequently, the AAO template containing the PMMA structures was bonded to a 0.25-mm thick PMMA sheet with epoxy resin (ITW Devcon, Ill.). Then the Al and AAO template was removed with a saturated aqueous solution of mercuric chloride, followed by 0.6 M phosphoric acid. (While mercuric chloride is currently the preferred oxidizing agent for this step, other oxidizing agents that are not proton sources may also be used.) Finally, the PMMA nanostructures were carefully washed with 18 MΩcm water, and the water was removed by freeze drying at −80° C.

Example 3. Preparation of Polymer Nanotubes

The AAO template was prepared by a two-step anodization process, followed by removal of the Al support with saturated aqueous mercuric chloride for 5-24 h. Subsequent dissolution of the oxide barrier-layer with 6% wt. $H_3PO_4$ at 40° C. for 30 min yielded AAO templates possessing nanochannels with both ends open. A piece of 0.25-mm thick polymer sheet, either PMMA (Goodfellow, Devon, Pa.) or COC (Topas 6013D61 Advanced Polymers GmbH, Florence, Ky.), was placed in contact with the anodic aluminum oxide surface. The assembly was then clamped together between two glass microscope slides using binding clips (ACCO, Lincolnshire, Ill.). The polymer was melted by heating at 230° C. for 10 min under vacuum (170 Pa) in a standard vacuum oven. The polymer/AAO composite was then cooled to room temperature and removed from the glass slide support by soaking the assembly in an ultrasonic water bath. The AAO template pattern was dissolved in 0.6 M $H_3PO_4$ solution at ambient temperature. The erect polymer nanotubes were obtained by washing with Nanopure water (Barnstead, 18 MΩ-cm) followed by freeze-drying removal of the water using a Labconco FreezeZone Freeze Dry System. The nanotubes can be advantageous in that they provide even further increased surface area.

Example 4. Effect of Degassing

In initial tests on early prototypes, we observed that the PUHARNs were shorter in length than the nanochannels of the AAO replication templates. Without wishing to be bound by this hypothesis, we attributed the difference to gases trapped in the nanochannels. We used ultrasonication to degas the channels during fabrication of nanopillars, followed by high vacuum to degas the AAO nanopores. This treatment practically eliminated back pressure when the liquids subsequently wetted and flowed into the channels, resulting in PUHARNs of the expected lengths, without significant shortening.

Example 5. Effect of Freeze-Drying

In other initial tests, we had observed that after the AAO was removed with aqueous NaOH and then air dried following the methods described in prior reports on fabricating CdS nanowires, block copolymer nanotubes, and metallic nanotubes (e.g., W. Lee et al., *Langmuir* 2004, 20, 7665-7669; H. Xiang et al., *Macromolecules* 2004, 37, 5660-5664; Y. Liang et al., *J. Am. Chem. Soc.* 2004, 126, 16338-16339; W. Lee, *Angew. Chem. Int. Ed.* 2005, 44, 6050-6054), the polymeric high-aspect-ratio nanopillars/nanotubes routinely collapsed into an entangled mesh or clusters. SEM images of such samples demonstrated that PMMA nanopillars collapsed, and nanotubes congregated into 1-2 μm bundles clustered into disordered domains. Without wishing to be bound by this hypothesis, we attributed the observed collapse to surface tension forces acting on the nanopillars/nanotubes during the evaporation of the rinse liquid. On the scale of the nanopillars or nanotubes, the force due to surface tension is considerable. Modeling a nanostructure as a lever, the force F acting on a nanostructure in contact with an evaporating rinse liquid of given surface tension γ is proportional to the pillar or tube's aspect ratio A, inversely proportional to the interpillar spacing d, and proportional to the cosine of the contact angle θ of the rinse liquid at the nanopillar/nanotube surface: F∝Aγ(cos θ)/d. To reduce this force, the surface tension could be reduced, or the contact angle of the rinse liquid with respect to the nanostructures could be brought close to 90° (cos θ=0). We have discovered that the latter can be accomplished by simple freeze-drying removal at −80° C. of the liquid in contact with the PUHARNs, instead of supercritical drying. The surface tension drops essentially to zero as the liquid freezes, avoiding problems from surface tension effects. Either freeze-drying or supercritical drying may be used to remove the solvent. Supercritical drying also results in the gradual reduction of surface tension to zero.

Example 6. Effect of Choice of Etching Agent

We also found that NaOH is not a good choice for the removal of AAO to obtain ordered, erect, ultra-high-aspect-ratio nanopillars. When NaOH (10%, w/w) was used without freeze-drying, the resulting nanopillars were severely deformed, twisted bundles. We discovered that free-standing nanopillars could be produced with high aspect ratios, at least up to 1,667 (100 μm height, 60-nm diameter), when $H_3PO_4$ was instead used to remove the template. Without wishing to be bound by this hypothesis, we attributed this phenomenon to the relatively hydrophobic surface of the PMMA nanopillars at low pH resulting from unionized carboxylic acid groups. During the polymerization of methyl methacrylate under 254-nm light, some photo-oxidation of the resulting PMMA also occurs, leading to surface carboxylic acid groups. In addition, we have found that commercial polymer sheets have varying degrees of surface carboxylic acids present, presumably as the result of photo-induced oxidation from their exposure to ambient conditions. Due to the differing wettabilities of carboxylic acids and carboxylate ions, the contact angle of water on the surface is a function of solution pH. Thus, when NaOH is used to remove the AAO template, the carboxylic acids on the surface of PMMA nanopillars are fully ionized to carboxylate ions, and the adhesive force between the water and the PMMA surface increases; the contact angle of water on the PMMA surface becomes quite low. By contrast, nearly all surface carboxylic acid groups are protonated when $H_3PO_4$ is instead used to remove the AAO template; the contact angle of water and the PMMA surface increases, and the force from surface tension is much weaker.

By both using dilute $H_3PO_4$ to remove the AAO template and using freeze-drying to remove solvent, the surface tension forces are greatly reduced between individual nanopillars/nanotubes for a variety of polymeric materials, including PMMA, COC, and the vast majority of alternative polymers previously mentioned.

Large-area, erect, free-standing polymeric nanopillar/nanotube arrays have been routinely formed with the novel method. A preferred configuration for the PUHARNs in many applications will be a hexagonal packing, but square packing and other configurations may also be used.

The lengths of the nanopillars/nanotubes that we have been produced have been quite uniform, and were equal to the thickness of the original AAO template (within measurement error).

Example 7. Very High Aspect Ratios

Typical dimensions for nanopillars/nanotubes that we have manufactured to date were 175 nm diameter, edge-to-edge spacing of 285 nm, height 1 μm or 60 μm, aspect ratio 6 or 343. These dimensions may readily be modified by altering the anodic oxidation conditions used to form the nanoporous AAO template (electrolyte, current, voltage, etc.) We have also made higher aspect ratio structures, up to ~1600.

Examples 8 and 9. Swelling of Nanotubes, and Alternative Polymers

In another embodiment, we manufactured free-standing PMMA nanotubes having a wall thickness of 50 nm, a height of 60 μm, and an outer diameter of 232 nm. The outer diameter was larger than the channel diameter of the AAO template, 175 nm, which we attributed to the "die swell" property of viscoelastic polymers. Similar results and dimensions were obtained with Topas 6013D61, a cyclic olefin copolymer (COC).

Examples 10 and 11. Conditions Favoring Nanotubes, and Conditions Favoring Nanopillars Our experiments found that nanotubes were formed when we used either a polymer melt or a polymer solution (polymer dissolved in solvent), while nanopillars were formed when we used a monomer solution followed by in situ polymerization. Without wishing to be bound by the following hypotheses, we propose that the underlying mechanisms may be as follows:

The mechanisms depend on the interactions of the liquids with the template, as well as the properties of the liquids themselves. Our hypothesis is that the formation of nanotubes or nanopillars depends on surface wetting and on the rheology of viscoelastic fluids.

Due to the high surface energy of AAO (1340 mN m$^{-1}$ for γ-$Al_2O_3$), organic materials with a low surface energy (<100 mN m$^{-1}$), including certain polymers, will spread onto and completely wet AAO surfaces. A nm-thick layer of the low-surface-energy material (precursor film) will form when the equilibrium spreading coefficient, S, is zero, where S=$\gamma_{sv}$−$\gamma_{s1}$−$\gamma_{1v}$ ($\gamma_{sv}$, $\gamma_{s1}$, and $\gamma_{1v}$ denote the solid-vapor, solid-liquid, and liquid-vapor surface tension values, respectively). The precursor film emanates from a macroscopic-sized droplet of liquid and spreads onto the high-surface-energy template due to the surface pressure exerted by the liquid at the solid/vapor interface. While the thickness of the precursor film can approach almost a millimeter, in the vicinity of the microscopic spreading front the thickness typically ranges from less than 100 nm down to several Angstroms. A mesoscopic film forms when the solution of low-surface-energy organic material spreads along the walls of the template nanopores in a manner analogous to the formation of the precursor films on flat substrates. In the case of a viscous fluid, after the mesoscopic film is formed, fluid starts to fill the nanochannels via sink-like flow resulting from Laplacian capillary pressure (P=2γ cos θ/R, where θ is the contact angle, γ the surface tension, and R the pore radius) associated with the meniscus curvature of the liquid. This capillary pressure tends to pull the liquid into the template nanochannels, while the liquid's inertia and friction oppose the capillary pressure-induced movement.

For viscoelastic flow of a high-surface-energy liquid into nanochannels, the Weissenberg effect inherent in Poiseuillean flow and the spring effect in the converging stream at the nanochannel entrance should be taken into account. In steady-shear flow, there exist stresses along the stream line flow, perpendicular to the flow, and vertical to the flow. For Newtonian fluids, these stresses are equal to one another and to the hydrodynamic pressure. For polymer melts, tensile normal stresses develop along streamlines, and compressive normal stresses develop perpendicular to the flow, which result in a rod-climbing, curvilinear flow that is known as the Weissenberg effect. This climbing effect results from the combination of the unequal normal forces and the curvature of the shearing surfaces. In Poiseuillean flow (a parabolic velocity profile), elastic inclusions of the fluid are stretched due to velocity gradients, giving rise to an extra stress directed counter to the flow. The Weissenberg effect causes a reduction in Laplacian capillary pressure at the meniscus, leading to a weakening of the driving force. In sink-like flow at the nanochannel inlet, the velocity gradients also cause stretching of elastic inclusions, and the effective restoring force (spring strain) pulls the meniscus backward as the meniscus propagates inside the nanochannel. This effect is called the spring effect.

For the case of polymer melts, the restoring force caused by the spring effect in a converging flow is pronounced and hinders the flow of polymer melt into the nanochannels, and as a result the meniscus is pulled back. The nanotubes that result from polymer melts originate from mesoscopic films formed along the wall of the nanochannels of the template. For polymer solutions, the spring effect is not great enough to prevent solution entering into the nanochannels. However, the Weissenberg effect plays an important role in slowing solution flow into the nanochannels. Due to solvent volatility, the solvent evaporates from the inside of the nanochannels, leaving polymer on top of the existing mesoscopic film inside the channel walls. This mechanism explains why the wall thickness of a nanotube derived from polymer solution is a function of polymer concentration.

For monomer solutions, the spring and Weissenberg effects inherent in viscoelastic fluids are small in comparison to the capillary force produced from surface tension. Thus, monomer solution can fill the entire volume of the nanochannels, and subsequent photopolymerization of monomer then leads to production of polymeric nanopillars rather than nanotubes.

The free-standing nanopillars/nanotubes we have made have exhibited very good mechanical and chemical properties. They have been exposed to aqueous solutions for extended periods of time (days) without showing signs of structural deformation or collapse.

Example 12. Incorporation of Arrays into Integrated Systems

The novel free-standing polymeric nanostructures (nanopillars or nanotubes) may be integrated into polymer-based microfluidic devices. Such devices are particularly well suited for applications employing mixed-scale structures. Microfluidic channels may be filled with nanostructure arrays serving as bioreactors, extraction beds, separation beds, or the like.

We have demonstrated the robustness of embodiments of nanopillar arrays. We have shown that microfluidic devices with integrated nanopillars can successfully be used repeatedly without loss of function. Additionally, the surface of the PUHARNs can be chemically modified without harm to the underlying nanostructures, allowing the attachment of a variety of chemical and biological agents.

Examples 13 and 14. Surface Activation of Nanostructures

We caused carboxylic acid groups to form on the surfaces of the PMMA nanopillars, without significant changes in the nanopillars' shape or integrity. The nanopillars were irradiated with UV in an $O_2$ environment (ambient air), by exposure to 254-nm light, 15 mW cm$^{-2}$, ~20 min (total dose ~18 J cm$^{-2}$). The UV-modified PMMA nanostructures were then incubated with an aqueous solution containing 0.6 mg mL$^{-1}$ 1-ethyl-3-(3-dimethylaminopropyl)-carbodiimide (EDC), and 0.4 mg mL$^{-1}$ N-hydroxysuccinimide (NHS) in 100 mM HEPES buffer (pH 7.3) for 30 min at room temperature. To remove non-covalently attached species, the surface was then extensively rinsed with deionized water. The structures then remained immersed in water.

During this process, EDC reacted with the photogenerated carboxyl groups to form an amine-reactive intermediate, O-acylisourea. This intermediate reacted with NHS to form a stable amine-reactive NHS ester.

We have also used a direct-write, 20-min. UV exposure to photochemically pattern pendant surface carboxylic acids onto nanopillars. The surface density of the resulting carboxyl groups was a function of exposure time (as measured by XPS). SEM images of some of the smallest nanopillar feature sizes revealed little or no damage for exposure times up to at least 20 min, the approximate time at which carboxylic acid surface density saturated in this system. See FIG. 7. In addition, their surfaces exhibited higher water wettability, as the contact angle decreased from 99°±2° to 44°±2° following 20-min exposure. Higher wettability is beneficial in promoting the penetration of water-soluble molecules into the three-dimensional networks.

Nanopillars with activated surface carboxylic acid groups were also reacted with amine-containing materials (proteins, oligonucleotides). The solvent was subsequently removed by freeze-drying. SEM imaging of these functionalized nanopillars did not show signs of physical damage.

Example 15. Two-Dimensional Electrophoresis

In one embodiment, a PMMA microchip was used to provide highly-efficient, 2D electrophoretic protein separations. The chips may be re-used many times, perhaps 10-30 times or more. The number of times a chip may be re-used depends on the particular reactions and reaction conditions in which it is employed. For example, SDS μ-CGE and MEKC have been used in a prototype embodiment as the separation modes for the first and second separation dimensions, respectively. These separations were conducted in perpendicular, intersecting microchannels. Effluents from the first (SDS μ-CGE) dimension were transferred into the second dimension for approximately 0.5 seconds, followed by an electrophoresis run in the second (MEKC) dimension for approximately 10 seconds. Optionally, this two-stage cycle can be iterated to produce a temporally-interleaved analyte stream that is easily mappable, and hence interpreted, in a format similar to that provided by conventional 2D gel electrophoresis techniques. See FIGS. 4A, 4B, and 4C as examples. The analysis took approximately 12 min, compared to about 36 hours for a comparable separation using conventional techniques. It produced similar peak resolution, and showed a peak capacity of approximately 1,000. In future embodiments, improved peak capacity will be obtained by incorporating nanostructures into the first separation dimension of an otherwise similar microchip.

Example 16. Microchip Fabrication

Poly(methylmethacrylate), PMMA, from MSC (Melville, N.Y.) was selected for these embodiments because of its favorable physical and chemical properties, including high optical clarity at 632.8 nm, minimal replication errors following hot embossing, high separation efficiency, good migration time reproducibility, and suitable wettability. Using techniques that are otherwise well-known in the art, microfluidic channels were embossed into PMMA using a brass master mould insert fabricated by high-precision micro-milling. FIG. 1 depicts schematically the layout of a prototype micro-electrophoresis chip used for our 1D and 2D separations. The microchip channel lengths were 5 mm for each injection leg, 40 mm for the SDS µ-CGE dimension, and 25 mm for the MEKC separation dimension. All channels were 20 µm wide and 50 µm deep.

Example 17. Samples and Reagents

Alexa Fluor® 633 (excitation/emission=633/652 nm) conjugated proteins, including wheat germ agglutinin (WG, 38 kDa), actin (AC, 43 kDa), ovalbumin (OV, 45 kDa), protein A (PA, 45 kDa), streptavidin (ST, 53 kDa), bovine serum albumin (BSA, 66 kDa), *Helix pomatia* lectin (HPA, 70 kDa), transferrin (TR, 80 kDa), concanavalin A (CO, 104 kDa), and lectin peanut agglutinin (PNA, 110 kDa) were purchased from Molecular Probes Inc. (Eugene, Oreg.). Fluorescent labeling conjugation reactions were carried out by following the manufacturer's protocols, using a 1.5:1 dye-to-protein molar ratio. Dye-labeled protein solutions were prepared in 150 mM phosphate-buffered saline (PBS), pH 7.2 (Sigma, St. Louis, Mo.), with 2 mM sodium azide (Sigma, St. Louis, Mo.), and stored at 4° C. until used. For long term storage, the protein conjugates were divided into 100 µL aliquots and stored at −20° C. Protein mixtures were prepared in the desired concentrations by adding 12 mM TRIS/HCl, 0.1% w/v (3.5 mM) SDS, pH 8.5 (Beckman, Fullerton, Calif.) with 0.05% w/v methyl hydroxyethyl cellulose, MHEC (Sigma), which was used as a dynamic coating to suppress electroosmotic flow (EOF) in PMMA. The solutions were heated to 95° C. for 4 min to denature the proteins. SDS µ-CGE was performed with a SDS 14-200 matrix (Beckman, Fullerton, Calif.) and 12 mM TRIS/HCl, 0.1% w/v (3.5 mM) SDS, pH 8.5 as run buffer. Both the sieving matrix and the run buffer in the SDS µ-CGE separations contained 0.05% w/v MHEC to suppress EOF. MEKC was carried out with 12 mM TRIS/HCl, 0.4% w/v (14 mM) SDS, pH 8.5, containing 0.05% w/v MHEC. Additional SDS (Sigma) was added to the TRIS/HCL buffer to adjust the SDS concentration above the critical micelle concentration (cmc) (~0.24% w/v or ~8.4 mM in water, and somewhat less in buffer solutions) for the MEKC separations. Prior to use in the microchip, all solutions were filtered with a 0.2 µm Nylon-66 membrane filter (Cole-Parmer Instrument Co., Vernon, Ill.) and degassed (10 min). Protein solutions were centrifuged for 5 min at 6000 rpm to remove particulates. Mixtures of proteins with a total concentration of 30 nM were used for all 1D and 2D electrophoretic separations.

Example 18. LIF Detection and Electrophoresis Power Supply

Fluorescence was detected at positions $d_1$, $d_2$, and $d_3$ (see FIG. 1) of the microchip using an instrument constructed in-house. High-voltage for electrophoresis was applied to the reservoirs of the microchip with six independently-controlled power supplies. The program for data acquisition and power supply control was created using National Instruments LabVIEW software. The LabVIEW controller program is capable of importing user-defined parameters for separation and detection, including electrophoresis voltages and duration, sampling and switching times between reservoirs and channels, and measuring fluorescence intensity.

Example 19. Microchip Operation

The microfluidic chips were cleaned with a 0.01% w/v sodium azide solution in nano-pure water. Prior to each use, each microchip was rinsed by filling all reservoirs with 2 mg/mL MHEC dissolved in PBS, pH 7.2, and applying vacuum to reservoir 6 (see FIG. 1) for at least 10 min at room temperature to suppress EOF, while keeping the chip immersed. A 5 min electrophoretic pre-run was performed with the separation buffers prior to each electrophoresis run to obtain a stable current during the separations. Peak identities were confirmed through migration time matching by injecting the analytes individually.

Examples 20 and 21. One Dimensional Separations

All electrophoretic separations were carried out at ambient temperature in reverse mode (detection end anodic). Individual 1D SDS µ-CGE and MEKC separations were evaluated using 1-2 and 3-4 paths as injection and separation channels, respectively. The LIF detection positions for 1D separations were at points $d_2$ for SDS µ-CGE and $d_1$ for MEKC (see FIG. 1) to provide effective separation lengths of 30 and 10 mm, respectively. These 1D separations were used to evaluate separation performance for each dimension and also to evaluate orthogonality between the two dimensions.

Example 22. Two-Dimensional Separations

To perform an effective 2D separation, it is important to be able to introduce and, as much as possible, isolate two different separation media within the individual dimensions of the fluidic network. In this embodiment, the sieving matrix was filled between reservoir 3 and point $d_2$ only. To accomplish this, the SDS µ-CGE channel (3-4 channel) was filled with the sieving matrix using a plastic syringe from reservoir 3 and applying vacuum to reservoir 4 while reservoirs 5 and 6 were sealed. Matrix movement was monitored with an optical microscope. The filling process continued until the sieving matrix reached point $d_2$. Then the MEKC buffer was introduced into the MEKC channel from reservoir 6 with a syringe, and all reservoirs were sealed, except that 4 and 5 were left open to the atmosphere. This procedure not only filled the MEKC channel with the appropriate run buffer, but it also removed any extra sieving matrix in the MEKC channel. Excess sieving matrix in reservoirs 1 and 3 was carefully removed and replaced with sample or SDS μ-CGE run buffer. Finally, to obtain a smooth sieving matrix/solution interface and also to ensure proper buffer composition in each channel, a two-step electrokinetic run was performed, just prior to the 2D separation, by applying +0.8 kV and +0.5 kV to reservoirs 3 and 6, respectively, and grounding the remaining reservoirs. Then the polarity of reservoirs 3 and 6 was switched, and reservoirs 3 and 6 were electrophoresed again. Each step continued for ~3 min. The sieving matrix-filled microchip was checked by adding fluorescein (Sigma, $\lambda_{excitation}$=465-495 nm, $\lambda_{emission}$=520 nm) into the matrix and using a fluorescence microscope (Nikon EFD-3, Optical Apparatus, Ardmore, Pa.) to image the matrix/solution interface.

For both the 1D SDS μ-CGE and MEKC separations, after pressure-filling the channels with the sieving matrix or with run buffer, the sample reservoir (reservoir 1) was filled with the protein mixture and the other reservoirs were filled with run buffer. Injection into the 1-2 channel was initiated by applying a positive voltage (0.20 kV) to the sample waste reservoir (reservoir 2) and grounding the sample reservoir (reservoir 1) for the time needed to completely fill the cross channel (reservoirs 3-6 were floated during injection). Injection was performed using an electric field of 200 V/cm. Following injection, a positive voltage was switched to reservoir 4, and reservoir 3 was grounded. Pull-back voltages (10-15% of applied voltage at reservoir 4) were applied to the sample and waste reservoirs (reservoirs 1 and 2). The electric fields used for SDS μ-CGE and MEKC separations were 350 V/cm and 400 V/cm, respectively. The measured currents were 11 μA and 9 μA for the SDS μ-CGE and MEKC dimensions, respectively. Ohm plots of applied electric field versus current for each dimension indicated insignificant Joule heating at the voltages used.

After introducing the appropriate separation media within the individual dimensions of the fluidic network, the laser beam for LIF detection was positioned at point $d_3$ for the 2D separation. The configuration provided an effective separation length of 30 mm for the first dimension and 10 mm for the second dimension. Table 1 presents the high voltage protocols used in the 2D separation. As shown in Table 1, the injection and run steps were the same as previously discussed. SDS μ-CGE was induced by applying +1.40 kV to reservoir 4, and grounding reservoir 3. Reservoirs 1 and 2 were held at +0.14 kV until the end of the run. Reservoirs 5 and 6 were floated during the SDS μ-CGE separation.

TABLE 1

High voltage protocol for 2D separations on prototype PMMA microchip. The reference numerals 1 to 6 refer to the reservoirs on the 2D platform depicted in FIG. 1.

| | Applied Voltage (kV)[1] | | | | | |
|---|---|---|---|---|---|---|
| | Step | | | | | |
| | 1 | 2 | 3 | 4 | 5 | 6 |
| Injection | G | +0.20 | F | F | F | F |
| SDS μ-CGE | +0.14 | +0.14 | G | +1.40 | F | F |
| Second, MEKC cycle | +0.14 | +0.14 | F | F | G | +1.00 |
| First to second sample transfer | +0.14 | +0.14 | G | +1.40 | F | F |

[1]G: grounded, F: floating.

Samples were transferred to the second dimension every 0.5 s run time during the first dimension separation, by applying +1.00 kV to reservoir 6 and grounding reservoir 5. This provided an electric field of 400 V/cm for MEKC in the second dimension. Following the 0.5 s sample transfer from the first to the second dimension, each MEKC cycle was performed for 10 s. During each MEKC cycle, the components in the SDS μ-CGE dimension were parked by grounding point 4 (see Table 1). After the 10 s run time, MEKC electrophoresis was paused for 0.5 s by floating points 5 and 6. This resulted in the movement of components from the SDS μ-CGE dimension into the junction between the separation dimensions (point $d_2$), and provided a new sample plug to be introduced into the second dimension (MEKC). In this serially-implemented 2D separation, the transfer/separation cycles were repeated until all bands from the first dimension were transferred into the MEKC dimension.

LIF data were collected continuously from the start of the SDS μ-CGE at point $d_3$ and a "separation landscape" was generated by dividing the temporal LIF signal into successive runs, each representing a MEKC cycle, using ImageJ 1.34 s (National Institute of Health, Bethesda, Md.) and TableCurve 3D 4.0 (Systat Software Inc., Point Richmond, Calif.) software.

To evaluate the orthogonality of the SDS μ-CGE and MEKC separation dimensions, and to compare the efficiency of the final 2D separation with its respective SDS μ-CGE and MEKC dimensions, individual 1D separations were performed using the fluorescently-labeled protein mixture described above.

Example 23. SDS μ-CGE Separation of Proteins

Figure 2A:
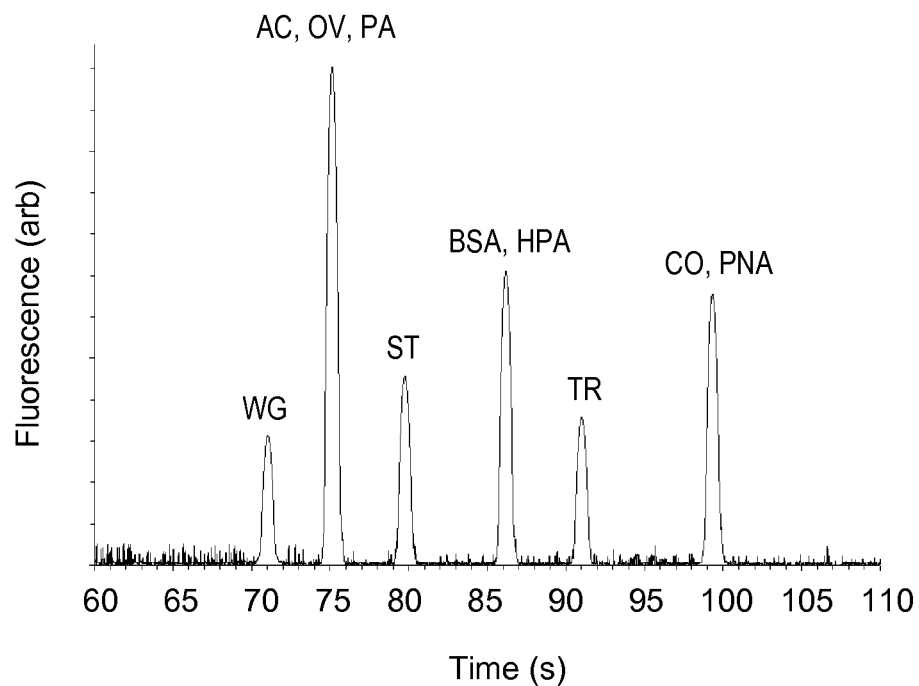
FIG. 2A depicts an SDS μ-CGE analysis (1D separation) of a 30 nM protein mixture using a PMMA microchip.

A SDS μ-CGE electropherogram taken with a PMMA prototype chip is shown in FIG. 2A. Electrophoresis was performed with an SDS 14-200 sieving matrix, 12 mM TRIS/HCl, 0.1% w/v (3.5 mM) SDS, pH 8.5, 0.05% w/v MHEC. Six peaks were present in the electropherogram. Three of the bands each included several co-migrating proteins with similar molecular weights: (i) AC, OV, and PA, (ii) BSA and HPA, and (iii) CO and PNA. Although separation efficiency (N) and thus resolution could be improved by increasing separation distance, proteins with similar molecular weights, such as OV and PA, will still not separate well using SDS μ-CGE. However, longer separation channels also increase separation time and sample dispersion due to diffusion, which can also increase due to geometrical spreading if the channel turns to maintain a compact footprint on the microchip. Also, filling long microchannels with highly viscous sieving matrices is difficult due to the high pressure drop across the channel. Thus simply increasing column length does not necessarily improve electrophoretic performance. However, incorporating nanostructures as an alternative should be beneficial.

Figure 2B:
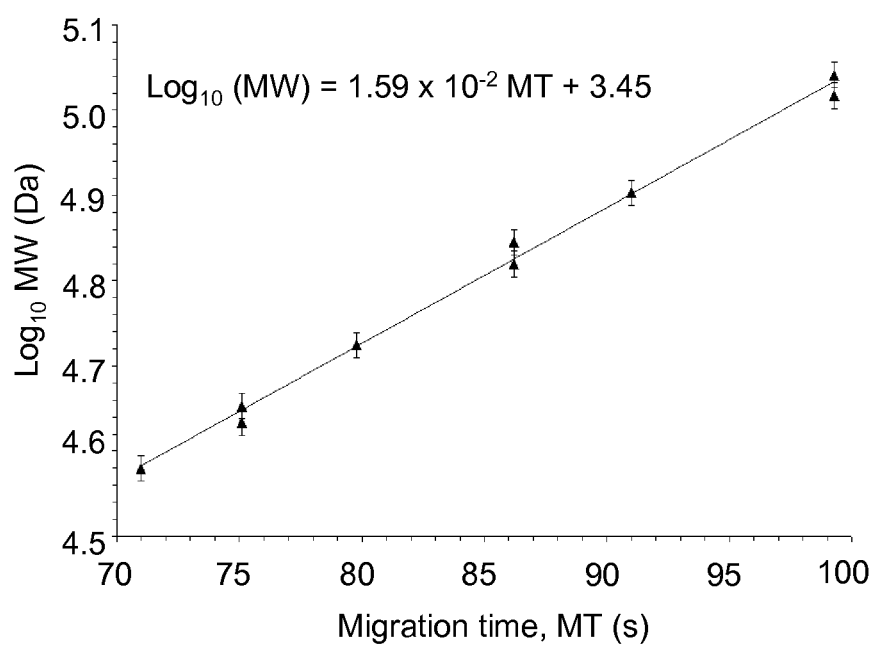
FIG. 2B depicts a plot of the logarithm of molecular mass versus migration time for the SDS μ-CGE separation of the labeled proteins shown in FIG. 2A. The proteins ranged in size from 38 to 110 kDa.

The average separation efficiency for the SDS μ-CGE electropherogram was calculated as $4.8 \times 10^4$ plates (plate height, H=0.62 μm). An apparent average resolution ($R_s$) of 2.8 was calculated, based on the spatial separation and peak width of the observed electrophoretic bands in the 1D separation, but disregarding the co-migration of some compounds. The peak capacity for the 1D separation was calculated as 19. FIG. 2B presents a linear plot of $\log_{10}(MW)$ versus migration times (MT) by SDS μ-CGE. The best linear fit for the data shown was:

$$\log_{10}(MW) = 1.59 \times 10^{-2} MT + 3.45 \qquad (1)$$

The plot showed good linearity ($R^2$=0.996) across the molecular weight range studied, 38-110 kDa. The SDS is believed to have contributed to the high linearity, acting not only to denature the proteins, but also to reduce any charge density differences among the proteins, which in turn should reduce potential variability in their partial specific volume and hydration.

Example 24. MEKC Separation of Proteins

We evaluated MEKC as the second dimension following SDS μ-CGE. The use of buffers containing micelles assists in separating proteins by CE via a hydrophobic or other protein/micelle interaction. The mechanism of separation is not well-understood for large molecules, particularly because larger molecules will not easily partition into a micelle's hydrophobic interior. However, different proteins may still experience differing degrees of denaturing/unfolding in the presence of micelles and surfactant monomers, which in turn may alter their frictional drag and electrophoretic mobility.

Eliminating or suppressing EOF helps decrease MEKC separation times, while preserving the selectivity of the separation, especially in the presence of anionic micelles. To reduce EOF, we used a dynamic coating of MHEC on the PMMA channels. (Methyl cellulose derivatives, e.g. MHEC, have minimal sieving properties at concentrations below ~0.1%.) The EOF measured for pristine PMMA was $1.6 \pm 0.05 \times 10^{-4}$ cm$^2$/V s. The EOF decreased by an order of magnitude, to $1.2 \pm 0.07 \times 10^{-5}$ cm$^2$/V s when MHEC was added to the MEKC run buffer.

Figure 3:
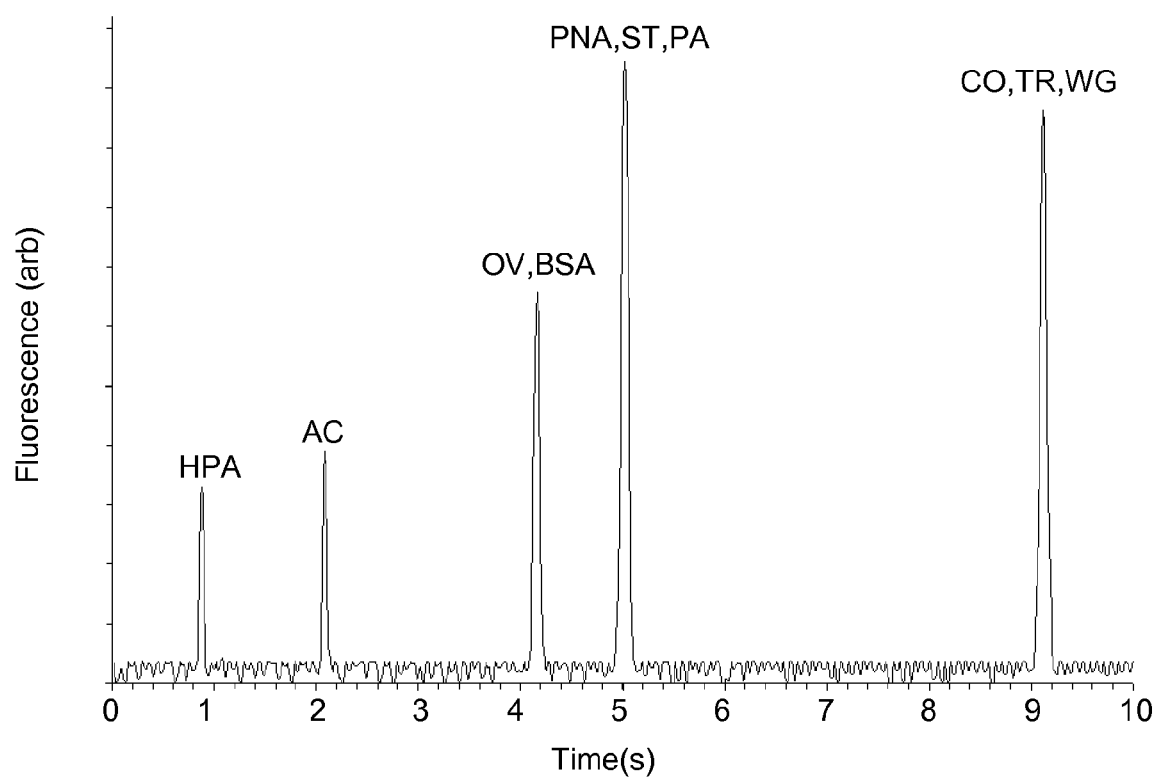
FIG. 3 depicts a 1D MEKC separation of a 30 nM protein mixture using a PMMA microchip.

MEKC runs of the protein mixture were performed using a shorter effective separation length than that used for SDS μ-CGE, to help decrease the development time. FIG. 3 depicts an MEKC electropherogram from a prototype PMMA microchip using 12 mM TRIS/HCl, 0.4% w/v (14 mM) SDS, pH 8.5, with 0.05% w/v MHEC as dynamic EOF suppressor. HPA, with a relatively high molecular weight (70 kDa), eluted first. On the other hand, WG eluted last despite its small molecular weight (38 kDa). Similar to SDS μ-CGE, groups of proteins (albeit different groups) co-migrated: OV-BSA, PNA-ST-PA, and CO-TR-WG.

Adding SDS to the run buffer can help better separate proteins, an effect that increases with increasing surfactant concentration. But increasing the SDS concentration also has the effect of increasing the MEKC separation window. In this set of experiments, increasing the SDS concentration did not eliminate the co-migration of the proteins studied. We also noticed that increasing the SDS concentration increased the buffer conductivity, producing higher current flow in the microchannel, and degrading separation performance due to excessive Joule heating effects. Finally, the high SDS concentration minimized protein transfer efficiency from the first to the second dimension when performing a 2D run. A preferred SDS concentration was set at 0.4% w/v (14 mM), well above its cmc. This concentration promoted high transfer efficiency from the first to the second dimension, while maintaining separation efficiency.

In MEKC, the average separation efficiency was calculated to be $1.2 \times 10^4$ plates (H=0.87 μm), peak width was 0.14 s, and peak capacity was 59. An apparent average resolution of 4.9 was calculated for the separation, (disregarding the co-migration of some proteins as previously described). The reproducibility of sample migration time depends on the chemical environment inside the separation channels. Poor migration time reproducibility and peak tailing in MEKC separations can result from high EOF or non-specific adsorption of proteins to the microchip wall. We attempted to minimize both EOF and protein non-specific adsorption with MHEC, and we obtained relatively high plate numbers for the MEKC dimension. The peaks in the MEKC electropherogram showed an average asymmetry factor (As) of $1.07 \pm 0.04$, indicating a lack of significant peak tailing, i.e., indicating relative low levels of potential solute/wall interactions.

Example 25. Two-Dimensional SDS μ-CGE×MEKC Separation of Labeled Proteins

It is important to properly sample components from the first dimension into the second dimension. For example, electrophoretic band aliasing due to low sampling into the second dimension should be minimized. Band aliasing can be reduced by employing a rapid analysis time in the second dimension, long development time in the first dimension, or both. We used SDS μ-CGE as the first separation dimension, because the development time of MEKC is much shorter than that of SDS μ-CGE. Another reason for selecting MEKC as the second separation dimension involved the consideration of diffusional contributions from each dimension. During each MEKC cycle, while protein bands from the first separation dimension are parked until transfer into the MEKC dimension, minimal amounts of diffusional spreading are expected. The sieving network significantly reduced diffusion of the proteins.

Example 26. Coupling SDS μ-CGE with MEKC

We coupled SDS μ-CGE with MEKC for a full 2D separation with the prototype PMMA microchip depicted in FIG. 1, with LIF detection at point d$_3$. Details of the injection and separation protocols are shown in Table 1. The time for starting the MEKC second dimension depended on the migration time of the smallest protein (or co-migrating proteins) from the SDS μ-CGE first dimension. The migration time could be estimated from Eq. 1. For the smallest protein in this mixture, WG, MW=38 kDa, Eq. 1 gives an estimated migration time MT ~71 seconds. Thus the first MEKC cycle was set to start at 70 s. (Alternatively, for a mixture containing components of unknown molecular weight, the run for the second dimension may be started by extrapolating the plot of FIG. 2B to 0 MT (~2.2 kDa), which essentially corresponds to the column holdup time.) The MEKC cycles were carried out by appropriate switching of the high voltage applied to points 5 and 6, as described previously. One "cycle" refers to one complete MEKC electrophoretic run, corresponding to the second dimension in the separation. In this case, because we observed that all proteins eluted from the MEKC channel within a 10 s separation window, the MEKC cycles were set at 10 s. For other protein mixtures, longer or shorter separation windows could be selected as appropriate.

Figure 4A:
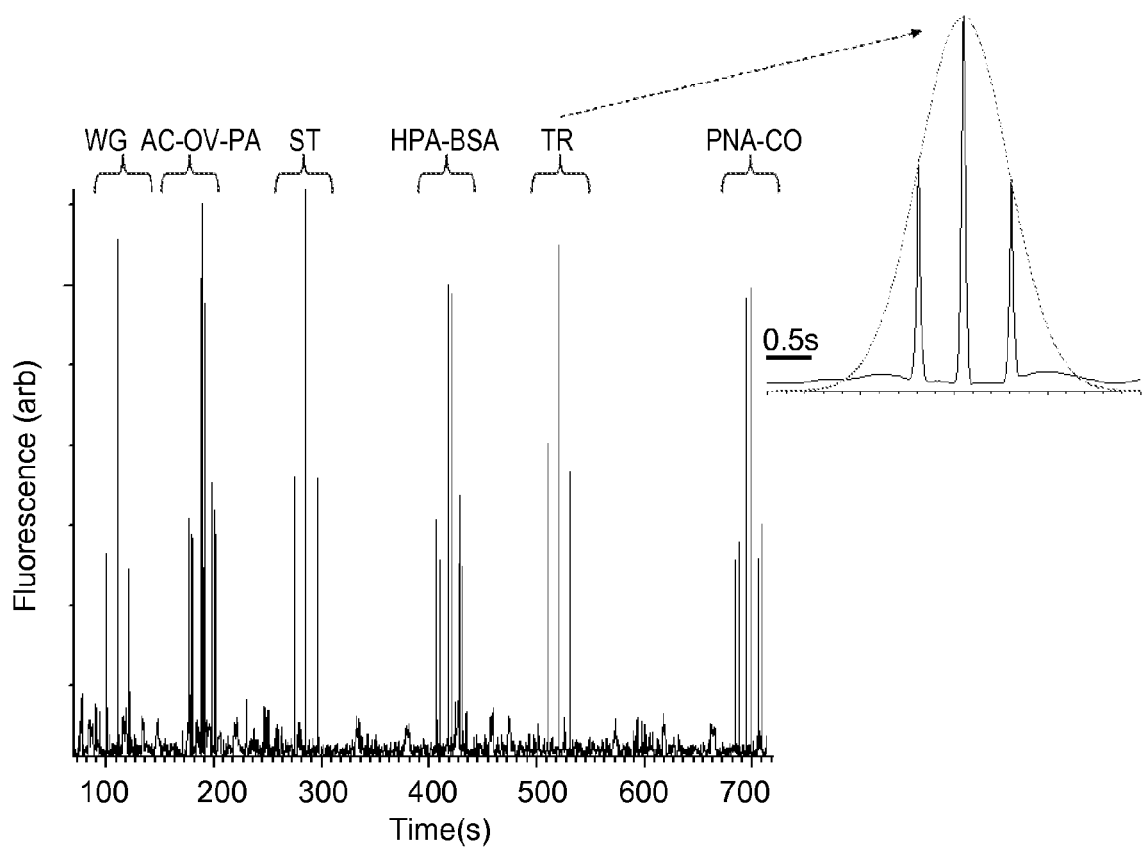
FIG. 4A depicts the linear output of a LIF 632.8 nm detector system from a 2D analysis of a protein mixture using a PMMA microchip.

FIG. 4A depicts the linear output of the detector from the 2D analysis of the protein mixture. Pulse injections (0.5 s) from the SDS μ-CGE peaks were taken, starting at 70 s, in channel 5-6. Separation conditions were the same as those for those depicted in FIGS. 2 and 3. The 2D analysis in FIG. 4A resolved all ten proteins in the mixture, including separating the co-migrating species that could not be separated in the individual 1D separations (FIGS. 2A and 3). The final 2D electropherogram was obtained from 61 MEKC cycles, following an initial SDS μ-CGE electrophoresis of 70 seconds.

An important consideration when separation dimensions are coupled serially is to minimize sample loss when making injections from the first dimension into the second dimension, while maintaining separation efficiency. In a comprehensive 2D system, the effluent from the first dimension is preferably sampled into the second dimension at regular intervals, with fixed volumes, and without being diluted or dispersed. To maintain continuity between the two dimensions, their respective buffers should preferably be the same, or as similar as possible, including their pH, concentration of MHEC (or other EOF suppressor), and the concentration of other buffer constituents. In our case, the run buffers were essentially identical except for SDS concentration (i.e., 0.1% and 0.4% w/v SDS for µ-CGE and MEKC, respectively). A higher concentration was used in the MEKC dimension to promote micelle formation, as previously discussed.

To maintain separation performance and minimize band aliasing, each peak from the first dimension should be sampled multiple times in the second dimension; our procedure used three such samples per peak. This "oversampling" from the first dimension into the second enhanced the overall separation performance of the 2D system. In these experiments, the average peak width just prior to the second dimension (point $d_2$, FIG. 1) produced by the SDS µ-CGE dimension was 1.52 s. Therefore, with a transfer time of 0.5 s, the average protein band eluting from the first dimension would be sampled about three times. FIG. 4A shows an expanded view of one band (TR) that was "oversampled," producing about 3 peaks in the linear electropherogram. Fitting these oversampled peaks to a Gaussian (and removing the 2 intervening MEKC cycles) gave a band width at the base of ~2.4 s, corresponding to about $7.2 \times 10^5$ plates for the 2D separation ($H_{TOT}$=0.056 µm).

The duration of the serially-coupled SDS µ-CGE and MEKC depended on the number of MEKC cycles, 61, the sample transfer time (0.5 s), the development time for each MEKC cycle (10 s), and the initial first dimension run time (70 s). The 2D separation of the proteins in this study was complete in about 12 min. Even shorter 2D separation times can be achieved by reducing the initial SDS µ-CGE development time, reducing the number of MEKC cycles, reducing the sample transfer time, or reducing the MEKC development time. The MEKC development time may be reduced simply by reducing the column length, but at the cost of a reduction in resolution. But, as noted in the MEKC 1D results, the apparent average resolution using a 10 mm length column (4.91) indicated that shorter columns would be feasible. If we assume that $R_s$ is proportional to $L^{1/2}$, and if we require $R_s$~1.5, then a 5 mm column length for the MEKC dimension should suffice, with a development time ~5 s. That should reduce the total separation time for the system to ~6-7 min. An additional advantage is that reducing the MEKC development time should also reduce the diffusional spreading contribution (HD) to the total plate height ($H_{TOT}$). In the data reported here, HD represented ~39% of $H_{TOT}$.

Figure 4B:
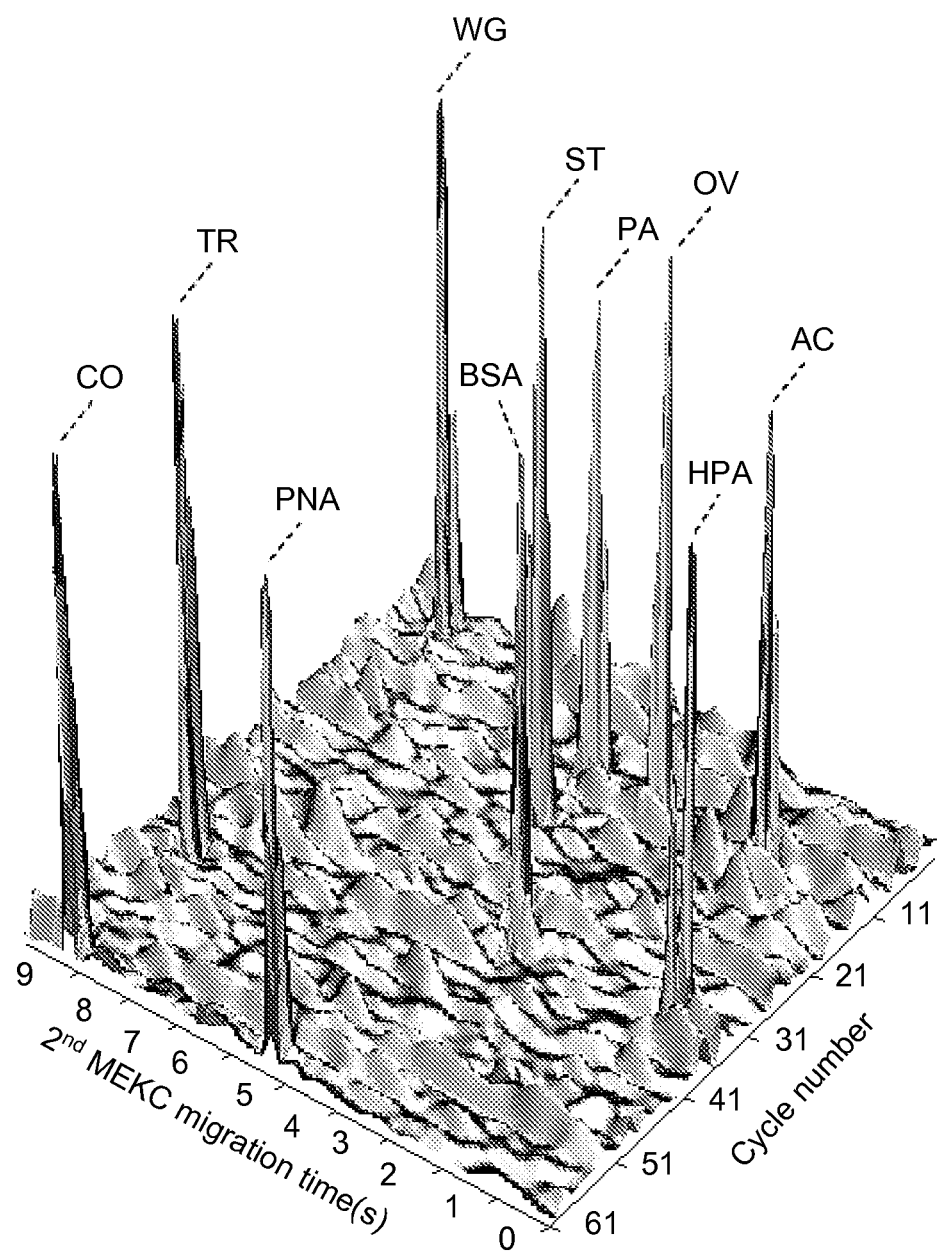
FIG. 4B depicts a three-dimensional image of the data from FIG. 4A, with the cycle number plotted versus the MEKC migration time.
Figure 4C:
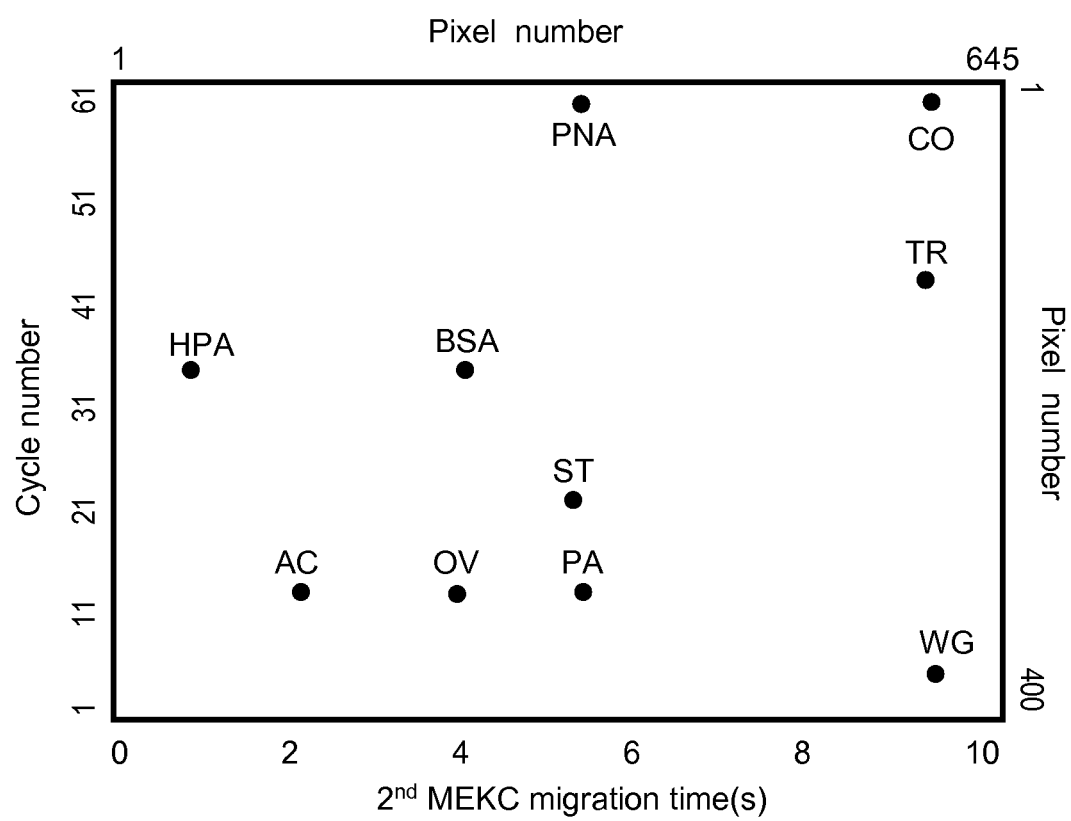
FIG. 4C depicts the data of FIG. 4B, re-formatted to resemble the appearance of a hypothetical, comparable, conventional stained gel.

The data from FIG. 4A were converted into a landscape projection, depicted in FIG. 4B; and also into an image resembling a conventional 2D stained gel, depicted in FIG. 4C.

The peak width from the first dimension may be used as an approximate measure for the width of the injection plug in the second dimension. It can be helpful to use separation channels with relatively narrow widths and relatively large depths. Narrower channels enhance peak capacity by reducing zone variances that can be introduced by a finite (or "bolus") injection plug in the second, MEKC dimension. A deeper channel can improve the detection limit by lengthening the effective detection path length. The average peak width for each MEKC cycle was 0.15 s±0.03 s, comparable to that for the 1D MEKC (0.14 s±0.02 s) runs. In the prototype microchip, with the samples we have tested, the sieving matrix and run buffers that we used provided highly reproducible migration times, high separation efficiencies, and rapid analysis times.

The benefit of a coupled 2D separation is readily seen by comparing its peak capacity to those of the constituent 1D separations. For our 1D SDS µ-CGE, the peak capacity was 19, while for MEKC it was 59. Therefore, the theoretical peak capacity of the 2D separation ($P_{2D}$) would be 1,121 (19×59). Actual peak capacity could be smaller due to an increase in peak width in the SDS µ-CGE dimension, for example due to protein diffusion during the MEKC separation, or cross-information from the individual separation dimensions.

The data shown in FIG. 4B were imported into ImageJ software to draw the representative 2D "simulated gel" image depicted in FIG. 4C. The separation resolving power can be derived from the number of pixels in each axis (x and y). As seen in FIG. 4C, the total area for the 2D analysis included 258,000 (400×645) pixels. With more MEKC cycles or longer MEKC development times, the 2D separation images will have more pixels. All 10 protein components from the sample were found in the 2D analysis. The average area for each component was 257.7 pixels. Assuming no free space between the protein spots, a maximum number of ~1,000 (258,000/257.7) elements could be determined in this 2D separation, in close agreement to the calculated theoretical peak capacity of 1,121.

The degree of orthogonality between the SDS µ-CGE and MEKC dimensions can be calculated from the data presented in FIG. 4C. The orthogonality (O) can be estimated as:

$$O = [\Sigma \text{bins} - \sqrt{P_{max}}]/[0.63 P_{max}] \quad (2)$$

where $\Sigma$bins is the number of bins (i.e., pixels) in the 2D plot containing data points (i.e., non-zero pixels), and $P_{max}$ is the total peak capacity obtained as a sum of all bins. Considering 8 bins that contained data points and a total capacity of 10, the orthogonality of this 2D system was calculated as 77% using Eq. 2. This value compared well to values reported previously (0%-69%) using a similar calculation method for different combinations of separation techniques to perform a 2D analysis (data not shown).

Practical peak capacity (Np) is usually lower than the theoretical peak capacity, because only a fraction of the 2D "surface" is actually used for separation in a particular situation. The practical peak capacity can be evaluated using the following equation;

$$N_p = P_{2D}[\Sigma \text{bins}]/P_{max} \quad (3)$$

Considering the values obtained above and using Eq. 3, Np=897 was determined for our 2D analysis using SDS-µCGE and MEKC.

The peak capacity and resolution could be further improved by reducing the size of each fluid sample introduced into the second dimension, by increasing the channel length in the first dimension, or by reducing sample dispersion during transfer between the first and second dimensions. In addition, using higher transfer frequencies from the first dimension into the second dimension can improve peak capacity, at the expense of increasing 2D electrophoresis development time.

All experimental data reported here were obtained using PMMA as the substrate. PMMA has favorable optical properties, permitting sensitive fluorescence readout. It is readily micromachined using techniques known in the art. Fabricating both separation channels in the same substrate (here, PMMA) also helped to minimize dead volumes between separation dimensions from interconnect pathways.

In future work, we will couple the output from the 2D separation system with on-line MS, or solid-phase proteolytic digestion, or both, to further improve the automated microfluidic processing of proteins.

Example 27. Solid-Phase Nanoreactors

A characteristic limitation on solid-phase reactions is the kinetic limit imposed by mass transfer of solution reagents to the solid phase, e.g., an immobilized enzyme. The polymer nanopillar ensembles can dramatically enhance the surface area available for reaction with the solid phase, without clogging the flow through microchannels. For example, the surface area of PMMA nanopillar ensembles with R=343 and 5.7 was approximately 181 and 4 times that of planar PMMA, respectively. The nanopillar ensembles can support a greater amount of enzyme, other catalyst, or solid-phase reagent in a given footprint on a chip; they facilitate the recycling of costly reagents; they can reduce diffusional barriers.

As an example, we found that the kinetic parameter $V_{max}$ for the digestion of N-benzoyl-L-arginine-p-nitroanilide to yield p-nitroaniline was ~10-times greater for trypsin covalently attached to PMMA UHARN (51.8 µM min$^{-1}$, R=343) as compared to planar PMMA (5.02 µM min$^{-1}$). This ability to process a large amount of solution-phase reactants over a given two-dimensional domain will be useful in flow-through bio-reactors or other reactors in microfluidic devices where high sample processing speeds are important.

Examples 28 and 29. Bioreactors Using Planar PMMA and PMMA Nanopillars

To fabricate a bioreactor containing active trypsin immobilized on a solid support, the UV-modified planar PMMA or PMMA nanopillar surface (prepared as described above) was soaked in 10 mL of trypsin, 1 mg mL$^{-1}$, in 100 mM HEPES buffer (pH 7.3) with 20 mM CaCl$_2$ for 20 h at 4° C. Non-immobilized trypsin was removed by rinsing the PMMA surface with HEPES buffer, followed by distilled water. The immobilized trypsin was stable and maintained its enzymatic activity for over 2 months at 4° C., even after repeated use. The amount of trypsin immobilized onto the planar PMMA and PMMA nanopillar surfaces was analyzed using the Biochinchoninic Acid (BCA) protein assay method. The assay found a load of 7.5 µg of trypsin immobilized onto a planar PMMA surface of 78.5 mm$^2$. The enzyme load onto the same lateral area, but with three-dimensional PMMA nanopillars having a diameter of 175 nm and an aspect ratio of 343, was found to be 81.5 g, representing an increased enzyme load of ~11 on the nanotextured surface.

Figure 8:
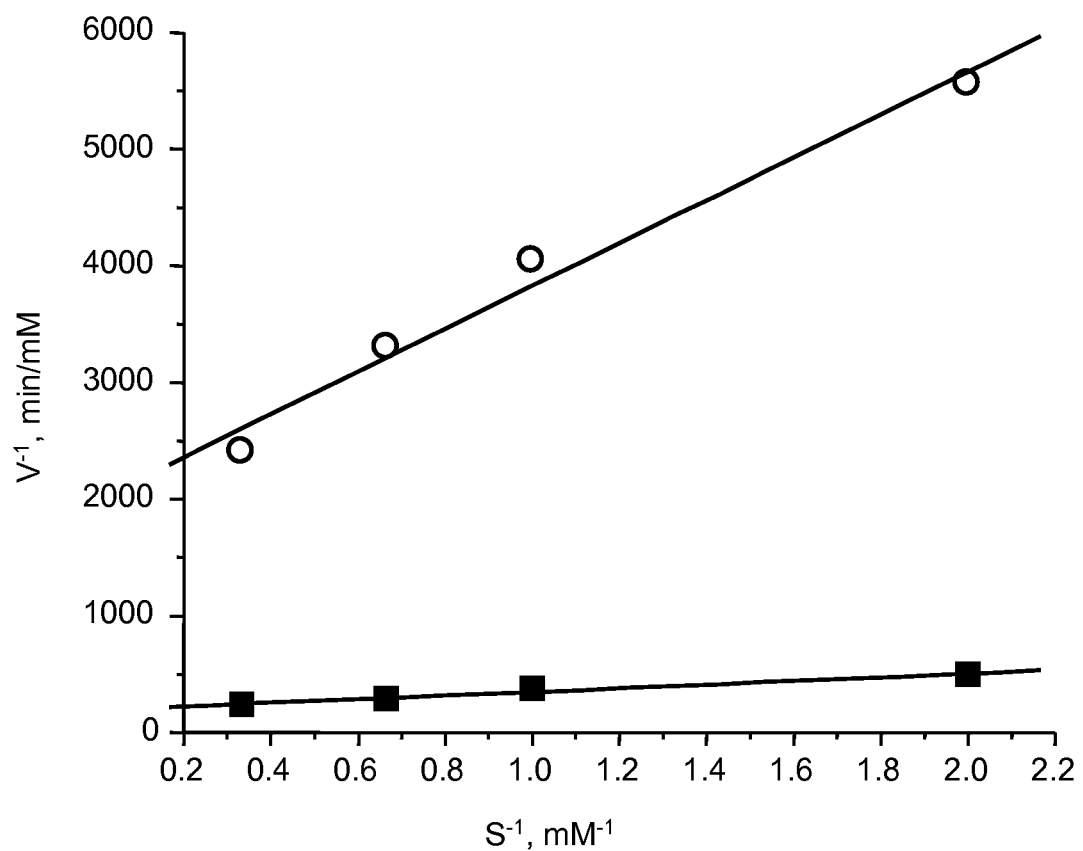
FIG. 8 depicts Lineweaver-Burke plots of immobilized trypsin on planar PMMA ■ and PMMA nanopillar ○ bioreactors.

We determined the activity of the trypsin immobilized onto the planar and nanopillar PMMA surfaces by observing the digestion of L-BAPNA (N-benzoyl-L-arginine p-nitroanilide) in the concentration range 0.5 to 3 mM in 100 mM Tris-HCl (pH 8.0) buffer containing 20 mM CaCl$_2$. A 2 mL solution containing L-BAPNA (volume=2 mL) was placed on the surface of both planar and nanotextured PMMA with the immobilized trypsin enzyme. The solid-phase reactor bed was surrounded by an O-ring and placed between two glass slides. The generated product, p-nitroaniline, was measured by absorbance spectrophotometry at 410 nm using a Cary 50 UV/Vis spectrophotometer (Varian Instruments, Walnut Creek, Calif., USA). The concentration of p-nitroaniline was calculated from a Beer's law plot with a molar absorptivity taken as 8800 L mol$^{-1}$ cm$^{-1}$. The initial reaction rate, $V_0$, was determined by finding the slope of a plot of product concentration versus time during the initial stages of enzymatic reaction, at each concentration tested. The data were plotted using the Lineweaver-Burke equation, as depicted in FIG. 8. The results gave values for $V_{max}$, the maximum velocity of reaction when the active sites of the enzyme were saturated with reactant. The values for $V_{max}$ were found to be 5.02 and 51.8 µM/min for planar and the nanopillar PMMA surfaces, respectively. These values were roughly proportional to the measured levels of immobilized enzyme load on the two types of surfaces. The value for $K_m$, (the Michaelis constant) was found to be 0.921 and 0.809 mM for nanotextured and planar PMMA surfaces, respectively.

Example 30. Nanostructured Bioreactors for Proteolytic Digestions

Figure 9A:
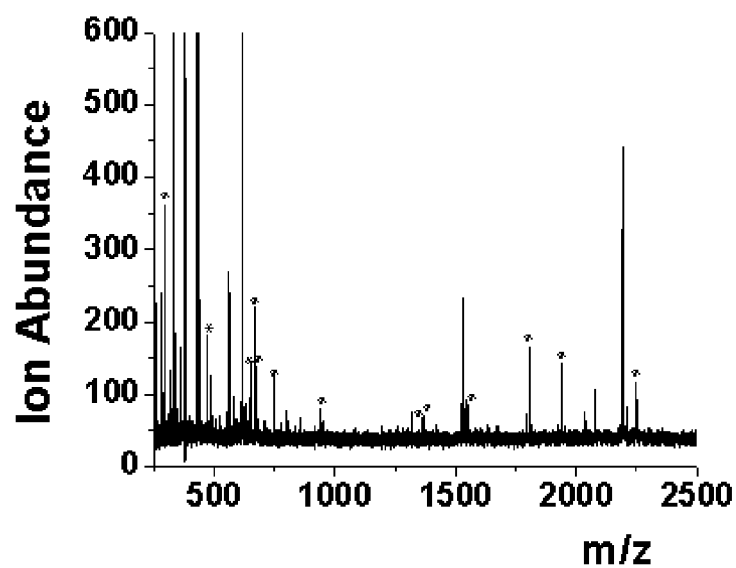
FIG. 9A depicts a MALDI-TOF mass spectrum from a trypsin digest of equine heart myoglobin, with the trypsin immobilized on PMMA nanopillars having an aspect ratio of 343. The peaks identified by asterisks * are those whose masses correspond to the expected trypsin digestion products.
Figure 9B:
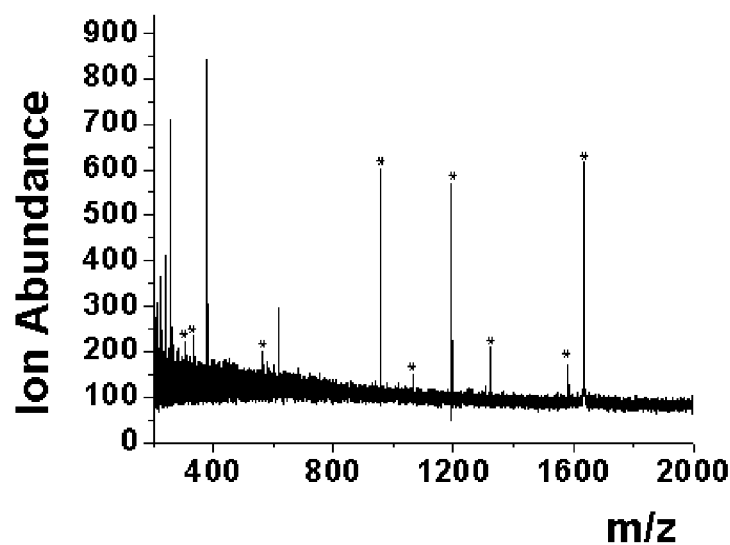
FIG. 9B depicts a MALDI-TOF mass spectrum from a trypsin digest of bovine heart cytochrome C, with the trypsin immobilized on PMMA nanopillars having an aspect ratio of 343. The peaks identified by asterisks * are those whose masses correspond to the expected trypsin digestion products.

We further demonstrated the utility of the novel nanotextured bioreactor by generating a solid-phase proteolytic digestion of proteins, followed by analysis of the peptide fragments by Matrix-Assisted Laser Desorption/Ionization Time-of-Flight Mass Spectrometry (MALDI-TOF MS). A preliminary evaluation of protein mapping was made with two proteins, myoglobin (equine heart) and cytochrome C (bovine heart). Prior to matrix addition, samples were acidified with TFA. The acidified tryptic digests were then analyzed by MALDI-TOF MS, with 10 mg/mL sinapinic acid in 70% acetonitrile and 0.1% TFA as the matrix. The resulting mass spectra were compared against a protein digestion database (Protein Prospector, rospectro.ucsf.edu) both to identify digest fragments and to estimate the degree of digestion. The mass spectra depicted in FIG. 9 indicate that 14 and 11 peptide fragments were identified from myoglobin and cytochrome C, respectively. Detailed results are given in Table 2 below. 105 out of 153 amino acids of myoglobin and 57 out of 104 amino acids of cytochrome C were acquired, corresponding to 68.6% and 54.8% sequence coverage, respectively.

TABLE 2

Solid-phase proteolytic digestions of myoglobin and cytochrome C, using either nanostructured or in-solution reactions.

| Protein | Myoglobin | | Cytochrome C | |
| --- | --- | --- | --- | --- |
| | Bio-reactor | In-solution | Bio-reactor | In-solution |
| Protein MW (Da) | 16,935 | 16,935 | 12,327 | 12,327 |
| Total amino acids | 153 | 153 | 104 | 104 |
| Digestion time (hr) | 1 | 6 | 1 | 6 |
| Amino acids identified | 105 | 80 | 57 | 79 |
| Sequence coverage (%) | 68.6 | 52.3 | 54.8 | 76 |
| Peptides matched | 14 | 9 | 11 | 17 |

Example 31. Fabrication of Polymeric Nanopillars Contained within Microfluidic Channels An AAO template was prepared on an aluminum support. An AUTOCAD drawing of the microfluidic network was then used to pattern the AAO layer, using a Kern MMP 2522 high-precision micromilling machine (Kern Micro-und Feinwerktechnik GmbH & Co. KG, Murnau, Germany). Micromilling was carried out at 40,000 rpm using 500 µm and 200 µm-diameter milling bits. A typical milling cycle comprised rough milling of the microstructures with the 500 µm-diameter milling bit, followed by fine milling with the 200 µm-diameter bit. The patterned AAO template was then cleaned with a mixture of polar solvents (H$_2$O/ethanol/acetone/chloroform/hexane, 1/1/1/1/1 v/v) in an ultrasonic bath. Then methyl methacrylate monomer (Fisher Scientific, Pittsburgh, Pa.) containing benzoin methyl ether (Fisher Scientific, Pittsburgh, Pa.), a cleavage-type free-radical photoinitiator, and 1% (w/v) PMMA beads was placed into the nanopores of AAO, assisted by ultrasound. Polymerization was conducted with 254 nm UV for 30 min. Subsequently, the AAO with the embedded, patterned PMMA was hot-embossed onto a PMMA substrate (60 mm×20 mm) cut from a PMMA sheet (Goodfellow, Devon, USA). The AAO mold with patterned PMMA was mounted on the PMMA sheet and placed into a hot-embossing machine (HEX02, JENOPTIK Microtechnik GmbH, Germany). The embossing chamber was evacuated, and the assembly was heated to 150° C. The mold insert and substrate were then pressed together with a force of 1,000 lb. (~4,400 Newton) for 5 min. While maintaining the same compression force, the assembly was then slowly cooled below the $T_g$ of PMMA, after which the pressure was removed. Following the hot-embossing, the aluminum support was removed from the assembly by reaction with saturated $HgCl_2$. Reservoirs were drilled into the ends of the embossed PMMA microchannels with a KrF laser system (Rapid×1000 Series, Resonetics, Inc., Nashua, N.H.), at a laser fluence at the workpiece of 10 $J/cm^2$ and a repetition rate of 50 Hz.

The PMMA microchannels were sealed by vacuum-assisted thermal bonding: (i) The hot-embossed PMMA piece was superimposed onto a 1 mm thick blank PMMA sheet (cover plate); (ii) the assembly was placed in a vacuum oven for 30 min at 110° C. under a pressure of −30 inch Hg, which led to tight bonding at the interface between the two PMMA sheets; (iii) the nanopillars contained within the microchannel were exposed to dilute phosphoric acid for removal of the AAO template, followed by freeze-drying.

Figure 7A:
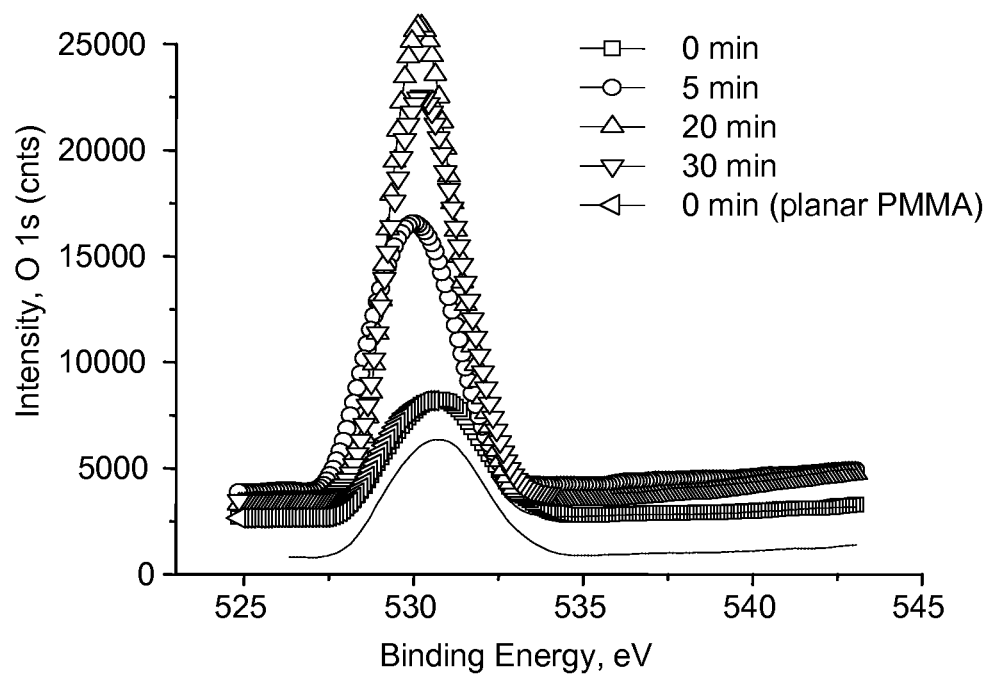
FIG. 7A depicts an X-ray photoelectron spectra illustrating the dependence of the UV modification time for the oxygen 1 s spectra of PMMA nanopillars.
Figure 7B:
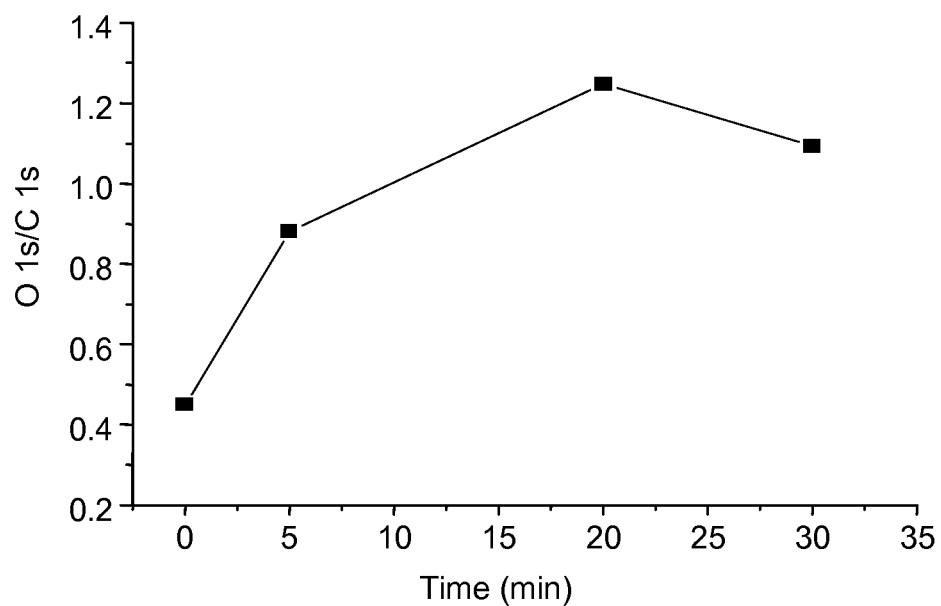
FIG. 7B depicts the relationship between the carbon 1 s and oxygen 1 s ratio and UV exposure time.

Example 32. XPS and Wettability Measurements (Water Contact Angle) on PMMA Nanopillar Arrays, Before and after UV Treatment Planar PMMA and PMMA nanopillar films were analyzed with an Axis 165X-ray Photoelectron Spectrometer (Kratos Analytical) using a monochromatized Al K X-ray (1486.6 eV) source at a power of 150 W. Survey and high-resolution spectra were taken using pass energies of 160 eV and 20 eV, respectively. The neutralizer was turned on during analysis to compensate for possible charge effects on the insulating polymer surfaces. FIG. 7 (a) depicts the results of the O 1 s region for the PMMA nanopillars with changes in the UV exposure time. The effect of UV exposure time on the ratio of oxygen atoms to carbon atoms is shown in FIG. 7 (b). The ratio of oxygen to carbon on the surface of the PMMA nanopillars increased as the UV irradiation time of the surface in air increased from 0 to 20 min, indicating the introduction of oxygen into the polymer during UV exposure. The introduction of oxygen was inferred to result primarily from the formation of carboxyl groups. However, as the UV exposure time was further increased to 30 min, the ratio of oxygen to carbon actually decreased, which we attributed to the collapse of nanostructures in response to increasing amounts of ionizing radiation. SEM images were consistent with this hypothesis, indicating that the PMMA nanopillars maintained their structural integrity following a 20-minute exposure. However, after a 30 minute UV exposure, the nanopillars showed significant collapse when viewed by SEM. Based on these results the preferred UV exposure time to functionalize a PMMA with carboxyl groups, under the conditions used in these exposures, was about 20 min.

The water contact angle (CA) on PMMA nanopillars was carried out using a VCA 2000 contact angle system equipped with a CCD camera (VCA, Billerica, Mass.). The manufacturer's software was used to obtain the contact angle values (average of 5 replicates, standard deviation of ±2° from a 2 µL sessile deionized water drop (18 MΩ-cm) placed on the surface being tested. As shown in FIG. 7, the surface of the as-synthesized PMMA nanopillars showed a contact angle of 99±2°. There was a significant increase in the wettability of the PMMA nanopillar surface as UV exposure time increased. After the preferred 20 min UV-exposure, the contact angle decreased to 44±2°, which we attributed to an increase in carboxylic acid group density.

The complete disclosures of all references cited in this specification, including without limitation the complete disclosure of the priority application, are hereby incorporated by reference. Any Internet-accessible supplemental materials that were published or otherwise made publicly available in association with any of the cited references are included within this incorporation by reference. In the event of an otherwise irreconcilable conflict, however, the present specification shall control.

What is claimed:

1. An integrated system for analysis of proteins and mixtures of proteins, wherein said system is contained on a single, monolithic microchip, said system comprising:
   (a) an input adapted to receive a sample and to deliver it to a solid-phase protein extractor;
   (b) a solid-phase protein extractor adapted to extract and concentrate proteins from the sample, and to output the extracted proteins to a first separation channel;
   (c) a first separation channel having a diameter less than about 100 µm, whose surface is adapted to separate the proteins by a first characteristic, wherein said first separation channel is adapted to output the separated proteins to a second separation channel;
   (d) a second separation channel having a diameter less than about 100 µm, whose surface is adapted to separate the proteins by a second characteristic, wherein said second separation channel is adapted to output the separated proteins to a solid-phase enzymatic reactor; wherein the first and second separation characteristics are substantially different;
   (e) a flow-through, solid-phase enzymatic reactor whose surface comprises one or more covalently-bound enzymes adapted to at least partially digest the separated proteins, and to output the digested proteins to a peptide separator; and
   (f) a peptide separator adapted to separate the peptide protein digest products by a third characteristic, wherein the third characteristic may be the same as the first or second characteristic, or different from both; and wherein said peptide separator is adapted to output the separated peptides to a detector;
wherein:
   (g) each of said solid-phase extractor, said enzymatic reactor, said first separation channel, and said second separation channel comprises an array of nanopillars having diameters between about 60 nm and about 500 nm, and aspect ratios 500 or higher, wherein said nanopillars comprise a synthetic polymer; wherein said nanopillars have solid interiors; and wherein said nanopillars are not hollow;
and wherein:
   (h) each said array of nanopillars is prepared by a process comprising the steps of:
      (i) supplying a template of anodic aluminum oxide, wherein at least one surface of the template has a shape complementary to the shape of at least one surface of the nanopillars to be made;
      (ii) impregnating at least the complementary surface of the template with a liquid comprising a solution of a polymer, or comprising a solution of a monomer precursor of a polymer, or comprising a polymer melt;

(iii) forming a solid polymer structure in the impregnated template by cooling the liquid or by inducing polymerization of monomer precursors in the liquid;

(iv) removing the template from the solid polymer structure; and (v) avoiding or reducing surface-tension-induced damage to the solid polymer structure by keeping it immersed in a liquid, or by removing residual liquid by freeze-drying, or by removing residual liquid by supercritical drying;

wherein:

(vi) the solid polymer structure that is produced comprises one or more arrays of intact nanopillars, wherein the nanopillars have diameters between about 60 nm and about 500 nm, and an aspect ratio that is 500 or higher.

2. The integrated system of claim 1, wherein the liquid comprises a solution of a polymer or a solution of a monomer precursor of a polymer, wherein the surface tension of the liquid causes the liquid to adhere to the surface of pores in the template, and whose viscosity is such that the interior of the pores fills, whereby the nanopillars formed comprise nanopillars with solid interiors.

3. The integrated system of claim 1, wherein the nanopillars have an aspect ratio that is at least about 1000.

4. The integrated system of claim 1, wherein the nanopillars have an aspect ratio that is at least about 1600.

5. The integrated system of claim 1, wherein said sample-receiving input additionally comprises a cell-lysis unit, a cell-selection unit, or both.

6. The integrated system of claim 1, wherein the surfaces of at least some of said nanopillars are chemically functionalized.

7. The integrated system of claim 1, wherein one or more of the first, second, and third characteristics is selected from the group consisting of microcapillary gel electrophoresis and micellar electrokinetic chromatography.

8. The integrated system of claim 1, wherein each of the first, second, and third characteristics is selected from the group consisting of microcapillary gel electrophoresis, and micellar electrokinetic chromatography.

* * * * *